US012716825B2

(12) United States Patent
Bredno et al.

(10) Patent No.: US 12,716,825 B2
(45) Date of Patent: Aug. 25, 2026

(54) METHOD OF STORING AND RETRIEVING DIGITAL PATHOLOGY ANALYSIS RESULTS

(71) Applicant: Ventana Medical Systems, Inc., Tucson, AZ (US)

(72) Inventors: Joerg Bredno, San Francisco, CA (US); Auranuch Lorsakul, Santa Clara, CA (US)

(73) Assignee: Ventana Medical Systems, Inc., Tucson, AZ (US)

( * ) Notice: Subject to any disclaimer, the term of this patent is extended or adjusted under 35 U.S.C. 154(b) by 102 days.

(21) Appl. No.: 18/592,400

(22) Filed: Feb. 29, 2024

(65) Prior Publication Data

US 2024/0201063 A1 Jun. 20, 2024

Related U.S. Application Data

(63) Continuation of application No. 18/146,881, filed on Dec. 27, 2022, now Pat. No. 11,959,848, which is a (Continued)

(51) Int. Cl.

| | |
|---|---|
| ***G01N 15/0227*** | (2024.01) |
| ***G01N 15/14*** | (2024.01) |
| ***G01N 15/1433*** | (2024.01) |
| ***G06K 1/00*** | (2006.01) |
| ***G06V 10/25*** | (2022.01) |

(Continued)

(52) U.S. Cl.

CPC ..... *G01N 15/0227* (2013.01); *G01N 15/1433* (2024.01); *G06K 1/00* (2013.01); *G06V 10/25* (2022.01); *G06V 10/763* (2022.01); *G06V 20/695* (2022.01); *G16H 10/40* (2018.01); *G16H 30/40* (2018.01); *G16H 50/70* (2018.01);

(Continued)

(58) Field of Classification Search

None

See application file for complete search history.

(56) References Cited

U.S. PATENT DOCUMENTS

| | | | |
|---|---|---|---|
| 10,018,631 | B2 | 7/2018 | Thorne et al. |
| 11,568,657 | B2 | 1/2023 | Bredno et al. |

(Continued)

FOREIGN PATENT DOCUMENTS

| | | | |
|---|---|---|---|
| CN | 103426169 | A | 12/2013 |
| CN | 107016684 | A | 8/2017 |

(Continued)

OTHER PUBLICATIONS

EP Application No. 18814573.4 , "Office Action", Dec. 10, 2024, 5 pages.

(Continued)

*Primary Examiner* — Jiangeng Sun

(74) *Attorney, Agent, or Firm* — Kilpatrick Townsend & Stockton LLP

(57) ABSTRACT

The present disclosure is directed, among other things, to automated systems and methods for analyzing, storing, and/or retrieving information associated with biological objects having irregular shapes. In some embodiments, the systems and methods partition an input image into a plurality of sub-regions based on localized colors, textures, and/or intensities in the input image, wherein each sub-region represents biologically meaningful data.

20 Claims, 20 Drawing Sheets
(16 of 20 Drawing Sheet(s) Filed in Color)

Related U.S. Application Data continuation of application No. 16/892,075, filed on Jun. 3, 2020, now Pat. No. 11,568,657, which is a continuation of application No. PCT/EP2018/083434, filed on Dec. 4, 2018.

(60) Provisional application No. 62/595,143, filed on Dec. 6, 2017.

(51) Int. Cl.

| | |
|---|---|
| ***G06V 10/762*** | (2022.01) |
| ***G06V 20/69*** | (2022.01) |
| ***G16H 10/40*** | (2018.01) |
| ***G16H 30/40*** | (2018.01) |
| ***G16H 50/70*** | (2018.01) |

(52) U.S. Cl.

CPC .. *G01N 2015/1497* (2013.01); *G06V 2201/03* (2022.01)

(56) References Cited

U.S. PATENT DOCUMENTS

| | | | |
|---|---|---|---|
| 11,959,848 | B2 | 4/2024 | Bredno et al. |
| 2003/0059093 | A1 | 3/2003 | Rosania et al. |
| 2007/0026525 | A1 | 2/2007 | Marcelpoil et al. |
| 2013/0130930 | A1 | 5/2013 | Parikh et al. |
| 2013/0226548 | A1 | 8/2013 | Beck et al. |
| 2015/0339818 | A1 | 11/2015 | Jain et al. |
| 2016/0335478 | A1 | 11/2016 | Bredno et al. |
| 2017/0091937 | A1 | 3/2017 | Barnes et al. |
| 2017/0262984 | A1 | 9/2017 | Barnes et al. |
| 2017/0323431 | A1 | 11/2017 | Sarkar et al. |

FOREIGN PATENT DOCUMENTS

| | | | |
|---|---|---|---|
| JP | 2006153742 | A | 6/2006 |
| JP | 2008104432 | A | 5/2008 |
| JP | 2009528835 | A | 8/2009 |
| JP | 2013540991 | A | 11/2013 |
| JP | 201 4533509 | A | 12/2014 |
| JP | 2015516985 | A | 6/2015 |
| JP | 2016503167 | A | 2/2016 |
| WO | 2005045734 | A1 | 5/2005 |
| WO | 2012043498 | A1 | 4/2012 |
| WO | 2012105281 | A1 | 8/2012 |
| WO | 2016150873 | A1 | 9/2016 |

OTHER PUBLICATIONS

U.S. Appl. No. 16/892,075, "Corrected Notice of Allowability", mailed on Jan. 4, 2023, 2 pages.

U.S. Appl. No. 16/892,075, "Non-Final Office Action", mailed on Jun. 17, 2022, 12 pages.

U.S. Appl. No. 16/892,075, "Notice of Allowance", mailed on Sep. 28, 2022, 6 pages.

U.S. Appl. No. 18/146,881, "Advisory Action", mailed on Oct. 23, 2023, 4 pages.

U.S. Appl. No. 18/146,881, "Final Office Action", mailed on Aug. 25, 2023, 11 pages.

U.S. Appl. No. 18/146,881, "Non-Final Office Action", mailed on Jun. 21, 2023, 10 pages.

U.S. Appl. No. 18/146,881, "Notice of Allowance", mailed on Jan. 10, 2024, 5 pages.

Achanta et al., "SLIC Superpixels Compared to State-of-the-Art Superpixel Methods", IEEE Transactions on Pattern Analysis and Machine Intelligence, vol. 34, No. 11, Nov. 2012, pp. 2274-2281.

CN Application No. 201880079402.1, "Notice of Decision to Grant", mailed on Jul. 1, 2023, 6 pages.

CN Application No. 201880079402.1, "Office Action", mailed on Feb. 3, 2023, 23 pages.

EP Application No. 18814573.4, "Office Action", mailed on Oct. 26, 2022, 4 pages.

Henry et al., "Clinical Implications of Fibroblast Activation Protein in Patients With Colon Cancer", Clinical Cancer Research vol. 13, No. 6, Mar. 15, 2007, 6 pages.

Jia et al., "NSLIC: SLIC Superpixels Based on Nonstationarity Measure", IEEE International Conference on Image Processing (ICIP),, Sep. 30, 2015, pp. 4738-4742.

JP Application No. 2020-530584, "Notice of Allowance", mailed on Nov. 18, 2022, 4 pages.

JP Application No. 2020-530584, "Office Action", mailed on Oct. 1, 2021, 15 pages.

JP Application No. 2020-530584, "Office Action", mailed on May 19, 2022, 4 pages.

JP Application No. 2022-200094, "Office Action", mailed on Nov. 17, 2023, 18 pages.

International Application No. PCT/EP2018/083434, "International Search Report and Written Opinion", Feb. 25, 2019, 11 pages.

JP Application No. 2022-200094 , "Office Action", Apr. 9, 2024, 11 pages.

JP Application No. 2022-200094 , "Notice of Allowance", Sep. 10, 2024, 6 pages.

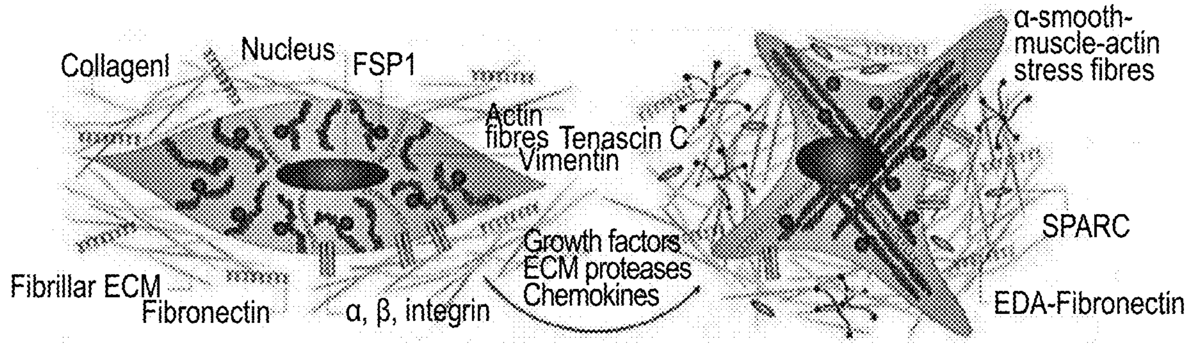
FIG. 5A
FIG. 5B
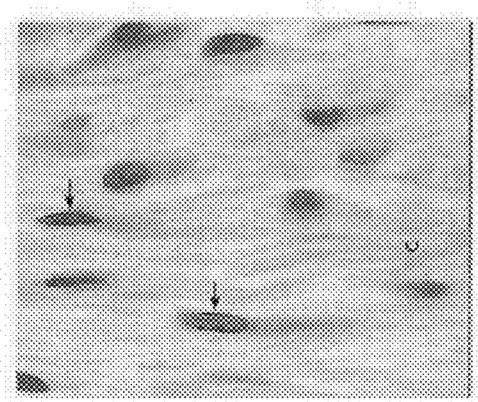
FIG. 5C
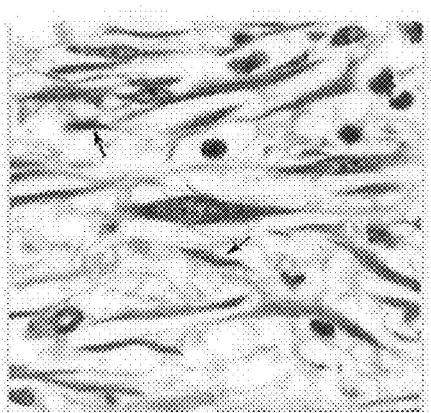
FIG. 5D

METHOD OF STORING AND RETRIEVING DIGITAL PATHOLOGY ANALYSIS RESULTS

CROSS REFERENCE TO RELATED APPLICATIONS

The present application is a continuation of U.S. application Ser. No. 18/146,881, filed Dec. 27, 2022, which is a continuation of U.S. application Ser. No. 16/892,075, filed on Jun. 3, 2020 (now U.S. Pat. No. 11,568,657), which is a continuation of International Application No. PCT/EP2018/083434 filed on Dec. 4, 2018, which application claims the benefit of the filing date of U.S. Provisional Patent Application No. 62/595,143, filed on Dec. 6, 2017, the disclosures of which are hereby incorporated by reference herein in their entireties for all purposes.

BACKGROUND OF THE DISCLOSURE

Digital pathology involves scanning of whole histopathology or cytopathology glass slides into digital images interpretable on a computer screen. These images are to be processed subsequently by an imaging algorithm or interpreted by a pathologist. In order to examine tissue sections (which are virtually transparent), tissue sections are prepared using colored histochemical stains that bind selectively to cellular components. Color-enhanced, or stained, cellular structures are used by clinicians or a computer-aided diagnosis (CAD) algorithm to identify morphological markers of a disease, and to proceed with therapy accordingly. Observing the assay enables a variety of processes, including diagnosis of disease, assessment of response to treatment, and development of new drugs to fight disease.

Immunohistochemical (IHC) slide staining can be utilized to identify proteins in cells of a tissue section and hence is widely used in the study of different types of cells, such as cancerous cells and immune cells in biological tissue. Thus, IHC staining may be used in research to understand the distribution and localization of the differentially expressed biomarkers of immune cells (such as T-cells or B-cells) in a cancerous tissue for an immune response study. For example, tumors often contain infiltrates of immune cells, which may prevent the development of tumors or favor the outgrowth of tumors.

In-situ hybridization (ISH) can be used to look for the presence of a genetic abnormality or condition such as amplification of cancer causing genes specifically in cells that, when viewed under a microscope, morphologically appear to be malignant. ISH employs labeled DNA or RNA probe molecules that are anti-sense to a target gene sequence or transcript to detect or localize targeted nucleic acid target genes within a cell or tissue sample. ISH is performed by exposing a cell or tissue sample immobilized on a glass slide to a labeled nucleic acid probe which is capable of specifically hybridizing to a given target gene in the cell or tissue sample. Several target genes can be simultaneously analyzed by exposing a cell or tissue sample to a plurality of nucleic acid probes that have been labeled with a plurality of different nucleic acid tags. By utilizing labels having different emission wavelengths, simultaneous multicolored analysis may be performed in a single step on a single target cell or tissue sample.

BRIEF SUMMARY OF THE DISCLOSURE

The present disclosure relates, among other things, to automated systems and methods for analyzing and storing data associated with biological objects having irregular shapes (e.g. fibroblasts or macrophages). The present disclosure also relates to automated systems and methods for analyzing and storing data associated with biological objects using a mid-resolution analysis (or medium-resolution analysis) approach, i.e. an approach that groups pixels having similar properties (e.g. staining intensity, staining presence, and/or texture) into "sub-regions."

In digital pathology, images are acquired from biological specimens (e.g., tissue specimens) mounted on a glass slide and stained for the identification of biomarkers. It is possible to assess the biological sample under a microscope at high magnification or to automatically analyze it with a digital pathology algorithm that detects and classifies biological objects of interest. For example, the objects of interest can be cells, vessels, glands, tissue regions, etc. Any derived information may be stored in a database for later retrieval, and the database may include statistics of a presence, absence, spatial relation, and/or staining properties of biological structures of interest. The skilled artisan will appreciate that the storage and retrieval of analysis results for clearly distinguished cells (e.g., tumor cells or immune cells) is relatively straightforward because such cells can be represented by a point at the center position of each cell and stored in a database (see, for example, FIG. 4). Similarly, biological objects of a well-defined size and shape (e.g., blood vessels) can be represented by a simple outline, where the coordinates of the outline can be stored in a database for later retrieval and/or further analysis (also referred to herein as a "polygon" or "polygon outline.")

On the other hand, some biological structures of interest, for example fibroblasts or macrophages, have an irregular shape. Groups of these types of cells may extend around each other or other cells (see FIG. 5). Consequently, it is often difficult to precisely identify these irregularly-shaped cells individually by an observer or by an automated algorithm. Instead, these cells are very often identified just by a local presence of their stained cytoplasm or membrane without the identification of individual cells.

While it may be possible to analyze and store such irregularly-shaped structures using a high-resolution analysis, such an approach often requires significant computer resources (compute time and or storage resources). Indeed, a high-resolution analysis approach that stores all pixel information of biological structures of interest (e.g., analysis results of every pixel) is believed to consume too many software and hardware resources (e.g., memory and processors to process or display the information) and, in the end, may not provide meaningful results for certain biological objects.

It may also be possible to analyze such irregular structures using a low-resolution analysis, where such a low-resolution data representation may "lump" several individual cells into a single object for storage in a database. By way of example, FIGS. 6A and 6B illustrate an example of an IHC images stained for tumor (yellow, 620) and fibroblasts (purple, 610), which are represented by a large polygon outline (red, 630) surrounding a group of relevant cells with exclusion "holes" (cyan, 640) for undesired regions. In this example, the analysis results are averaged over a large region (red outline, 630) that may contain a large number of individual cells having different features (e.g. shapes, sizes, staining intensities, etc.). For example, and with regard to FIG. 6B, the outlined fibroblast activation protein (FAP)-positive area, is 928.16 $um^2$ with a computed FAP-positive mean intensity of 0.26. Given the average intensity in such a large pixel area region, the mean intensity of 0.26 is quite coarse to indicate and be representative of the whole FAP-positive in this image. Without wishing to be bound by any particular theory, it is believed that this low-resolution analysis approach may lead to a loss of accuracy when stored results are subsequently utilized in downstream processing. As such, it is believed that due to such heterogeneity of the stained cells, this method does not locally present the actual detail of the regions of such biological structures of interest.

In contrast to the high-resolution and low-resolution analysis methods described above, the present disclosure provides systems and methods for deriving data corresponding to irregularly-shaped cells using a mid-resolution analysis approach by segmenting the image into a plurality of sub-regions, the sub-regions having similar image properties (e.g. at least one of texture, intensity, or color).

In view of the aforementioned, in one aspect of the current disclosure is a method of storing image analysis data derived from an image of a biological specimen having at least one stain comprising: (a) deriving one or more feature metrics from the image; (b) segmenting the image into a plurality of sub-regions, each sub-region comprising pixels that are substantially uniform in at least one of staining presence, staining intensity, or local texture; (c) generating a plurality representational objects based on the plurality of segmented sub-regions; (d) associating each of the plurality of representational objects with derived feature metrics; and (e) storing coordinates for each representational object along with the associated derived feature metrics in a database. The skilled artisan will appreciate that at least steps (a) and (b) may be performed in any order. In some embodiments, the segmentation of the image into the plurality of sub-regions comprises deriving superpixels. In some embodiments, the superpixels are derived by (i) grouping pixels with local k-means clustering; and (ii) using a connected components algorithm to merge small isolated regions into nearest large superpixels. Without wishing to be bound by any particular theory, it is believed that the superpixels (as sub-regions) are perceptually meaningful such that each superpixel is a perceptually consistent unit, i.e. all pixels in a superpixel are likely uniform in color and texture. In some embodiments, connected components labeling scans an image and groups its pixels into components based on pixel connectivity, i.e. all pixels in a connected component share similar pixel intensity values and are in some way connected with each other.

In some embodiments, the segmentation of the image into the plurality of sub-regions comprises overlaying a sampling grid onto the image, the sampling grid defining non-overlapping areas having a predetermined size and shape. In some embodiments, the sub-regions have a M×N size, where M ranges from 50 pixels to 100 pixels, and where N ranges from 50 pixels to about 100 pixels.

In some embodiments, the representational objects comprise outlines of sub-regions that meet a pre-defined staining intensity threshold. In some embodiments, representational objects comprise seed points. In some embodiments, the seed points are derived by computing a centroid for each of the plurality of sub-regions. In some embodiments, the derived feature metrics are staining intensities, and where an average staining intensity for all pixels within each generated representational object outline is computed. In some embodiments, the derived feature metrics are expression scores, and wherein average expression scores corresponding to areas within each generated sub-region are associated with the generated plurality of representational objects. In some embodiments, the method further comprises retrieving the stored coordinates and associated feature metric data from the database and projecting the retrieved data onto the image. In some embodiments, the analysis results (e.g., intensity, area) within a corresponding sub-region can be stored in the form of average pixel measurements which are representative of pixel data of that sub-region.

In some embodiments, the biological sample is stained with a membrane stain. In some embodiments, the biological sample is stained with at least one of a membrane stain and a nuclear stain. In some embodiments, the biological sample is stained with at least FAP, and wherein the derived one or more feature metrics include at least one of a FAP staining intensity or a FAP percent positivity. In some embodiments, an average FAP percent positivity is calculated for all pixels within a sub-region. In some embodiments, an average FAP staining intensity is calculated for all pixels within a sub-region. In some embodiments, the sample is stained with FAP and H&E. In some embodiments, the sample is stained with FAP and another nuclear or membrane stain.

In some embodiments, the images received as input are first unmixed into image channel images, e.g. an image channel image for a particular stain. In some embodiments, a region-of-interest is selected prior to image analysis.

In another aspect of the present disclosure is a system for deriving data corresponding to irregularly-shaped cells from an image of a biological sample comprising at least one stain, the system comprising: (i) one or more processors, and (ii) a memory coupled to the one or more processors, the memory to store computer-executable instructions that, when executed by the one or more processors, cause the one or more processors to perform operations comprising: (a) deriving one or more feature metrics from the image; (b) generating a plurality of sub-regions within the image, each sub-region having pixels with similar characteristics, the characteristics selected from color, brightness, and/or texture; (c) computing a series of representational objects based on the generated plurality of sub-regions; and (d) associating the derived one or more feature metrics from the image with calculated coordinates of each of the series of computed representational objects. In some embodiments, sub-regions are formed by grouping pixels that are (i) adjacent, (ii) have similar perceptually meaningful properties (e.g. color, brightness, and/or texture), are (iii) sufficiently homogenous with respect to biological properties (e.g. biological structures, staining properties of biological structures, cellular features, groups of cells). In some embodiments, pixels in a sub-region have similar properties and descriptive statistics for the biological objects of interest, e.g. irregularly shaped cells including, but not limited to, fibroblasts and macrophages.

In some embodiments, the segmentation of the image into the plurality of sub-regions comprises deriving superpixels. In some embodiments, the superpixels are derived using one of a graph-based approach or a gradient-ascent-based approach. In some embodiments, the superpixels are derived by (i) grouping pixels with local k-means clustering; and (ii) using a connected components algorithm to merge small isolated regions into nearest large superpixels.

In some embodiments, the representational objects comprise outlines of sub-regions that meet a pre-defined staining intensity threshold. In some embodiments, the representational objects comprise seed points. In some embodiments, the system further comprises instructions for storing the derived one or more feature metrics and associated calculated representational object coordinates in a database. In some embodiments, the one or more derived feature metrics comprise at least one expression score selected from percent positivity, an H-score, or a staining intensity. In some embodiments, data corresponding to irregularly-shaped cells is derived for a region-of-interest within the image. In some embodiments, the region-of-interest is an area of the image annotated by a medical professional.

In another aspect of the present disclosure is a non-transitory computer-readable medium storing instructions for analyzing data associated with biological objects having irregular shapes, the instructions comprising: (a) instructions for deriving one or more feature metrics from an image of a biological sample, the biological sample comprising at least one stain; (b) instructions for partitioning the image into a series of sub-regions by grouping pixels having similar characteristics, the characteristics selected from color, brightness, and/or texture; (c) instructions for computing a plurality of representational objects based on the series of partitioned sub-regions; and (d) instructions for associating the derived one or more feature metrics from the image with calculated coordinates of each of the plurality of computed representational objects.

In some embodiments, the partitioning of the image into the series of sub-regions comprising computing superpixels. In some embodiments, the superpixels are computing using one of a normalized cuts algorithm, an agglomerative clustering algorithm, a quick shift algorithm, a turbopixel algorithm, or simple linear iterative clustering algorithm. In some embodiments, the superpixels are generated using simple iterative clustering, and wherein a superpixel size parameter is set to between about 40 pixels and about 400 pixels, and wherein a compactness parameter is set to between about 10 to about 100. In some embodiments, the superpixels are computed by (i) grouping pixels with local k-means clustering; and (ii) using a connected components algorithm to merge small isolated regions into nearest large superpixels.

In some embodiments, the biological sample is stained with at least FAP, and wherein the derived one or more feature metrics include at least one of a FAP staining intensity or a FAP percent positivity. In some embodiments, an average FAP percent positivity is calculated for all pixels within a sub-region. In some embodiments, an average FAP staining intensity is calculated for all pixels within a sub-region. In some embodiments, the representational objects comprise at least one of polygon outlines and seed points. In some embodiments, the memory includes instructions for storing the derived one or more feature metrics and associated calculated representational object coordinates in a database. In some embodiments, the memory includes instructions for projecting stored information onto the image of the biological sample.

Applicants have shown that the systems and methods described herein provide an improved solution for storing analysis results of biological objects that cannot be defined by a single position or outline per object of interest. Moreover, applicants believe that the systems and methods disclosed herein allow for a reduction in storage space to store analysis results as compared with pixel-level, high-resolution analysis approaches, since analysis results of a particular pixel and its surrounding pixels are stored together in a sub-region, the pixels in the sub-region having similar properties or characteristics (e.g. color, brightness, texture). Applicants further believe that the systems and methods are computationally efficient since the generated sub-regions allow for a reduction in the complexity of images from several thousands of pixels to a smaller, more manageable number of sub-regions allowing for significantly faster further retrieval and reporting of analysis results. Applicants also believe that the sub-regions are representationally efficient since they are not too small or too large to store and represent analysis results. Finally, applicants submit that the systems and methods disclosed herein allow for enhanced accuracy, especially as compared with a low-resolution analysis approach, since the sub-regions generated describe properties or statistical information of biologically relevant objects of interest as compared with the storage of information from a larger regional representation (i.e. the sub-regions comprise pixels that are as uniform as possible in staining presence, staining intensity, and texture). These and other advantages are described further herein.

BRIEF DESCRIPTION OF THE FIGURES

The patent or application file contains at least one drawing executed in color. Copies of this patent or patent application publication with color drawing(s) will be provided by the Office upon request and payment of the necessary fee.

For a general understanding of the features of the disclosure, reference is made to the drawings. In the drawings, like reference numerals have been used throughout to identify identical elements.

FIGS. 5A-5D illustrate the appearance of fibroblast cells that are morphologically heterogeneous with diverse appearances (e.g. irregular size, shape, and boundary of cells). In the diagram, normal and activated fibroblasts are illustrated in (A) and (C), respectively. (C) and (D) set forth haematoxylin and eosin stained (H&E) images of normal and activated fibroblasts, respectively.

DETAILED DESCRIPTION

Figure 1:
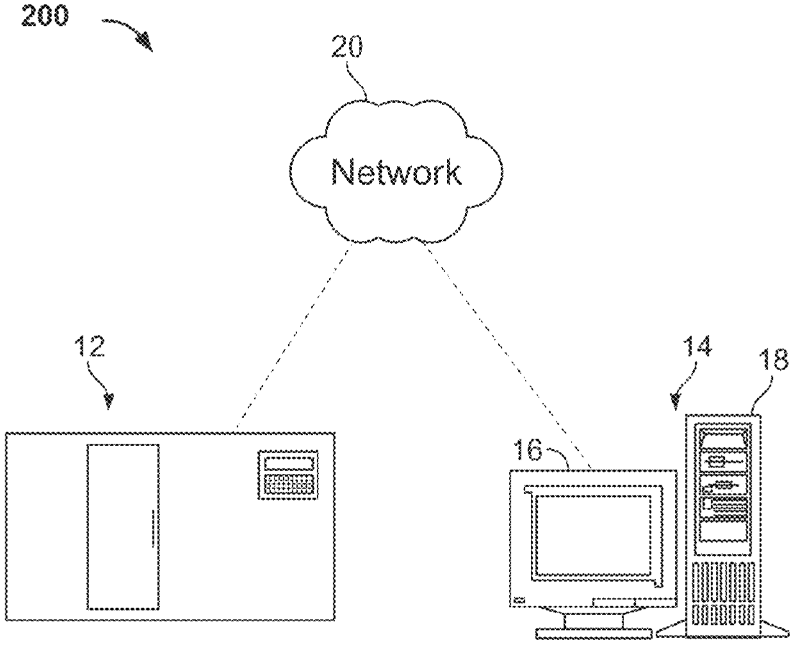
FIG. 1 illustrates a representative digital pathology system including an image acquisition device and a computer system, in accordance with some embodiments.

It should also be understood that, unless clearly indicated to the contrary, in any methods claimed herein that include more than one step or act, the order of the steps or acts of the method is not necessarily limited to the order in which the steps or acts of the method are recited.

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of." "Consisting essentially of," when used in the claims, shall have its ordinary meaning as used in the field of patent law.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the term "biological sample" (used interchangeably with the term "biological specimen" or "specimen" herein) or "tissue sample" (used interchangeably with the term "tissue specimen" herein) refers to any sample including a biomolecule (such as a protein, a peptide, a nucleic acid, a lipid, a carbohydrate, or a combination thereof) that is obtained from any organism including viruses. Other examples of organisms include mammals (such as humans; veterinary animals like cats, dogs, horses, cattle, and swine; and laboratory animals like mice, rats and primates), insects, annelids, arachnids, marsupials, reptiles, amphibians, bacteria, and fungi. Biological samples include tissue samples (such as tissue sections and needle biopsies of tissue), cell samples (such as cytological smears such as Pap smears or blood smears or samples of cells obtained by microdissection), or cell fractions, fragments or organelles (such as obtained by lysing cells and separating their components by centrifugation or otherwise). Other examples of biological samples include blood, serum, urine, semen, fecal matter, cerebrospinal fluid, interstitial fluid, mucous, tears, sweat, pus, biopsied tissue (for example, obtained by a surgical biopsy or a needle biopsy), nipple aspirates, cerumen, milk, vaginal fluid, saliva, swabs (such as buccal swabs), or any material containing biomolecules that is derived from a first biological sample. In certain embodiments, the term "biological sample" as used herein refers to a sample (such as a homogenized or liquefied sample) prepared from a tumor or a portion thereof obtained from a subject.

As used herein, the terms "biomarker" or "marker" refer to a measurable indicator of some biological state or condition. In particular, a biomarker may be a protein or peptide, e.g. a surface protein, that can be specifically stained, and which is indicative of a biological feature of the cell, e.g. the cell type or the physiological state of the cell. An immune cell marker is a biomarker that is selectively indicative of a feature that relates to an immune response of a mammal. A biomarker may be used to determine how well the body responds to a treatment for a disease or condition or if the subject is predisposed to a disease or condition. In the context of cancer, a biomarker refers to a biological substance that is indicative of the presence of cancer in the body. A biomarker may be a molecule secreted by a tumor or a specific response of the body to the presence of cancer. Genetic, epigenetic, proteomic, glycomic, and imaging biomarkers can be used for cancer diagnosis, prognosis, and epidemiology. Such biomarkers can be assayed in non-invasively collected biofluids like blood or serum. Several gene and protein based biomarkers have already been used in patient care including but, not limited to, AFP (Liver Cancer), BCR-ABL (Chronic Myeloid Leukemia), BRCA1/BRCA2 (Breast/Ovarian Cancer), BRAF V600E (Melanoma/Colorectal Cancer), CA-125 (Ovarian Cancer), CA19.9 (Pancreatic Cancer), CEA (Colorectal Cancer), EGFR (Non-small-cell lung carcinoma), HER-2 (Breast Cancer), KIT (Gastrointestinal stromal tumor), PSA (Prostate Specific Antigen), S100 (Melanoma), and many others. Biomarkers may be useful as diagnostics (to identify early stage cancers) and/or prognostics (to forecast how aggressive a cancer is and/or predict how a subject will respond to a particular treatment and/or how likely a cancer is to recur).

As used herein, the term "image data" as understood herein encompasses raw image data acquired from the biological sample, such as by means of an optical sensor or sensor array, or pre-processed image data. In particular, the image data may comprise a pixel matrix. As used herein, the term "immunohistochemistry" refers to a method of determining the presence or distribution of an antigen in a sample by detecting interaction of the antigen with a specific binding agent, such as an antibody. A sample is contacted with an antibody under conditions permitting antibody-antigen binding. Antibody-antigen binding can be detected by means of a detectable label conjugated to the antibody (direct detection) or by means of a detectable label conjugated to a secondary antibody, which binds specifically to the primary antibody (indirect detection). A "mask" as used herein is a derivative of a digital image wherein each pixel in the mask is represented as a binary value, e.g. "1" or "0" (or "true" or "false"). By overlaying a digital image with said mask, all pixels of the digital image mapped to a mask pixel of a particular one of the binary values are hidden, removed or otherwise ignored or filtered out in further processing steps applied on the digital image. For example, a mask can be generated from an original digital image by assigning all pixels of the original image with an intensity value above a threshold to true and otherwise false, thereby creating a mask that will filter out all pixels overlaid by a "false" masked pixel. A "multi-channel image" as understood herein encompasses a digital image obtained from a biological tissue sample in which different biological structures, such as nuclei and tissue structures, are simultaneously stained with specific fluorescent dyes, quantum dots, chromogens, etc., each of which fluoresces or are otherwise detectable in a different spectral band thus constituting one of the channels of the multi-channel image.

Overview

Applicants have developed a system and method of storing analysis results of biological objects having irregular shapes, including, for example, fibroblasts or macrophages in a database or other non-transitory memory. The analysis results may be subsequently retrieved from the database or memory for further analysis or for use in other downstream processes. The analysis results may also be projected onto input images or other derived images; or visualized by other means. In addition, the present disclosure also allows for the ability to adjust the size of generated sub-regions (e.g. by increasing or decreasing the size of a simple shape; or adjusting a parameter of a superpixels algorithm), facilitating the storage and reporting of analysis results with an adjustable level of detail. This is believed to allow for increased efficiencies and accuracies as compared with the low-resolution analysis approach described herein where an average analysis result from a global region of interest is saved.

As described further herein, the disclosed systems and methods are based on a mid-resolution analysis approach using locally similar small regions (sub-regions) to store analysis results. The sub-regions can be a simple shape (e.g., circle, square) or a complex shape (e.g., superpixels) and are utilized to store local analysis results of each small region across in an entire slide. The sub-regions defined by the present mid-resolution approach group pixels having similar (or homogeneous) properties (e.g. staining presence (i.e. the presence or absence of a particular stain), staining intensity (i.e. the relative intensity (or amount) of a stain), local texture (i.e. information about the spatial arrangement of color or intensities in an image or selected region of an image)), allowing for the identification of irregularly-shaped objects. In some embodiments, a sub-region within the mid-resolution approach has a size ranging from about 50 to about 100 pixels; or a pixel area between about 2,500 pixels$^2$ and about 10,000 pixels$^2$. Of course, the sub-region may have any size and the size may be based on the type of analysis being conducted and/or the type of cells being studied.

The skilled artisan will appreciate that a mid-level approach falls between the high and low-resolution analysis approaches described herein, such that data is collected on a sub-regional level, the sub-regions being smaller in proportion than the regions of interest in a low-resolution analysis, and obviously larger than a pixel as in a high-resolution analysis approach. By "high resolution analysis," it is meant image data captured at a pixel level or substantially at the pixel level. On the other hand, "low resolution analysis" refers to a regional-level analysis, such as a region having a size of at least 500 pixels by 500 pixels or an area having a size of greater than 250,000 pixels$^2$. The skilled artisan will appreciate that the low-resolution analysis approach would encompass many biological objects, e.g. a plurality of irregularly-shaped cells.

The present disclosure may refer to the analysis and storage of biological objects having irregular shapes and/or sizes, including fibroblasts or macrophages. It is to be understood that the present disclosure is not to be limited to fibroblasts or macrophages but may be extended to any biological object having a non-well-defined size or shape.

In the context of fibroblasts, fibroblasts are cells that make up the structural framework or stroma composed of the extracellular matrix and collagen in animal tissues. These cells are the most common type of connective tissue in animals and are important for wound healing. Fibroblasts come in various shapes and sizes, as well as in an activated and non-activated form (see, e.g. FIGS. 5A-5D). Fibroblasts are the activated form (the suffix "blast" refers to a metabolically active cell), while fibrocytes are considered less active. However, sometimes both fibroblasts and fibrocytes are not designated as being different and are simply referred to as fibroblasts. Morphologically, fibroblasts can be distinguished from fibrocytes by their abundance of rough endoplasmic reticulum and relatively larger size. Moreover, fibroblasts are believed to make contact with their neighbors, and the contacts are believed to be adhesions which may distort the form of the isolated cell. The mid-resolution analysis approach provided herein is able to account for these morphological differences and is believed to be well-suited to store information pertaining to fibroblasts, macrophages, and other irregular biological objects.

A digital pathology system 200 for imaging and analyzing specimens, in accordance with some embodiments, is illustrated in FIG. 1. The digital pathology system 200 may comprise an imaging apparatus 12 (e.g. an apparatus having means for scanning a specimen-bearing microscope slide) and a computer 14, whereby the imaging apparatus 12 and computer may be communicatively coupled together (e.g. directly, or indirectly over a network 20). The computer system 14 can include a desktop computer, a laptop computer, a tablet, or the like, digital electronic circuitry, firmware, hardware, memory, a computer storage medium, a computer program or set of instructions (e.g. where the program is stored within the memory or storage medium), one or more processors (including a programmed processor), and any other hardware, software, or firmware modules or combinations thereof. For example, the computing system 14 illustrated in FIG. 1 may comprise a computer with a display device 16 and an enclosure 18. The computer can store digital images in binary form (locally, such as in a memory, on a server, or another network connected device). The digital images can also be divided into a matrix of pixels. The pixels can include a digital value of one or more bits, defined by the bit depth. The skilled artisan will appreciate that other computer devices or systems may be utilized and that the computer systems described herein may be communicatively coupled to additional components, e.g. specimen analyzers, microscopes, other imaging systems, automated slide preparation equipment, etc. Some of these additional components and the various computers, networks, etc. that may be utilized are described further herein.

In general, the imaging apparatus 12 (or other image source including pre-scanned images stored in a memory) can include, without limitation, one or more image capture devices. Image capture devices can include, without limitation, a camera (e.g., an analog camera, a digital camera, etc.), optics (e.g., one or more lenses, sensor focus lens groups, microscope objectives, etc.), imaging sensors (e.g., a charge-coupled device (CCD), a complimentary metal-oxide semiconductor (CMOS) image sensor, or the like), photographic film, or the like. In digital embodiments, the image capture device can include a plurality of lenses that cooperate to prove on-the-fly focusing. An image sensor, for example, a CCD sensor can capture a digital image of the specimen. In some embodiments, the imaging apparatus 12 is a brightfield imaging system, a multispectral imaging (MSI) system or a fluorescent microscopy system. The digitized tissue data may be generated, for example, by an image scanning system, such as a VENTANA iScan HT scanner by VENTANA MEDICAL SYSTEMS, Inc. (Tucson, Arizona) or other suitable imaging equipment. Additional imaging devices and systems are described further herein. The skilled artisan will appreciate that the digital color image acquired by the imaging apparatus 12 can be conventionally composed of elementary color pixels. Each colored pixel can be coded over three digital components, each comprising the same number of bits, each component corresponding to a primary color, generally red, green or blue, also denoted by the term "RGB" components.

Figure 2:
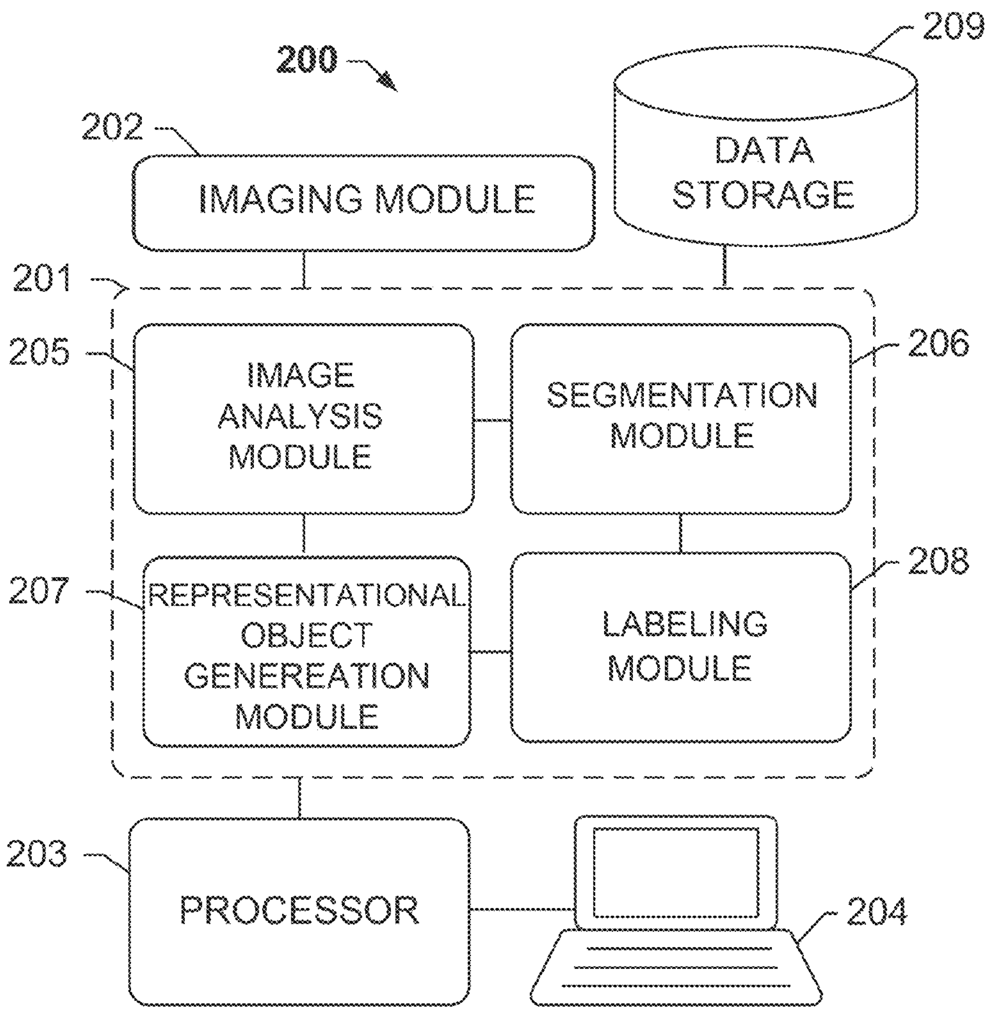
FIG. 2 sets forth various modules that can be utilized in a digital pathology system or within a digital pathology workflow, in accordance with some embodiments.

FIG. 2 provides an overview of the various modules utilized within the presently disclosed digital pathology system. In some embodiments, the digital pathology system employs a computer device 200 or computer-implemented method having one or more processors 203 and at least one memory 201, the at least one memory 201 storing non-transitory computer-readable instructions for execution by the one or more processors to cause the one or more processors to execute instructions (or stored data) in one or more modules (e.g. modules 202, and 205 through 209).

Figure 3:
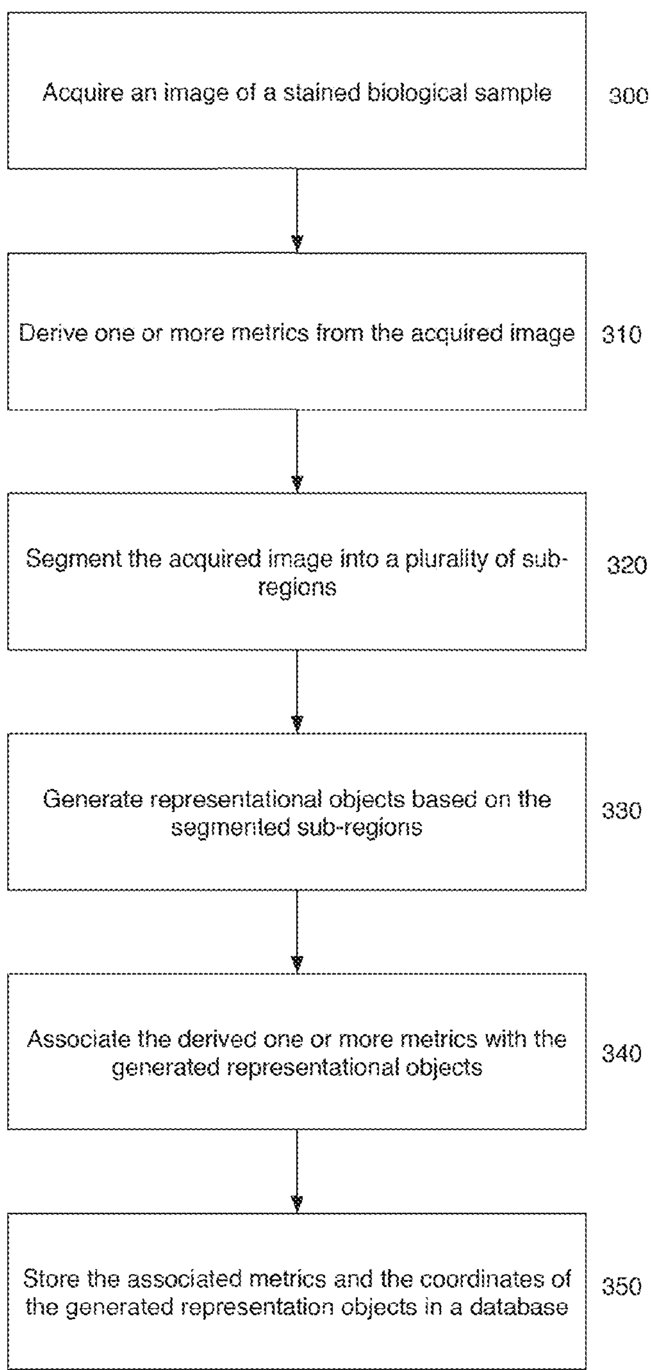
FIG. 3 sets forth a flowchart illustrating the various steps of deriving image analysis data and associated such image analysis data with generated sub-regions, in accordance with some embodiments.
Figure 4:
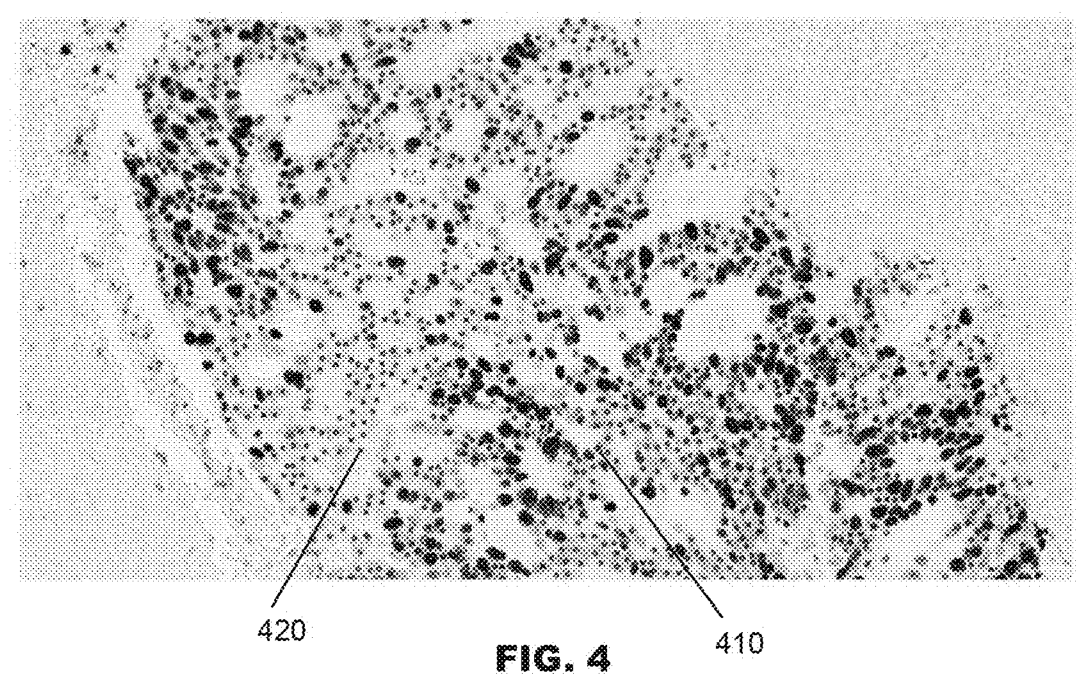
FIG. 4 provides an example of digital pathology image of liver cancer cells at a high-level resolution, in accordance with some embodiments. After image analysis processing and classification, the analysis results can be stored and retrieved from a database for display (e.g. as annotation points positioned at the center of the cell (Red=positive stained tumor cell (410), Green=negative stained tumor cell (420)). Each annotation point can contain read-out information e.g., descriptive statistics of the presence, absence, spatial relation, and staining properties of biological structures of interest.
Figure 6A:
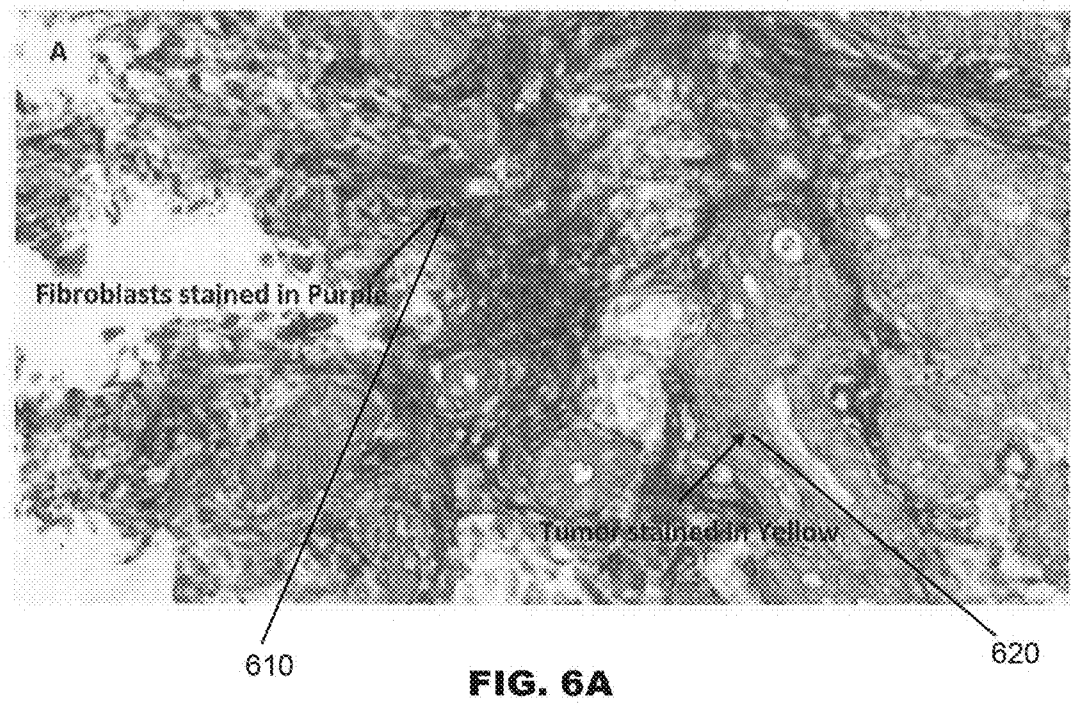
FIG. 6A sets forth an example of immunohistochemistry (IHC) of fibroblasts associated with tumor cells, where fibroblasts (610) are stained in purple and tumor (620) stained in yellow. As shown, fibroblasts can touch and have a very irregular shape, extending beyond or around other cells.
Figure 6B:
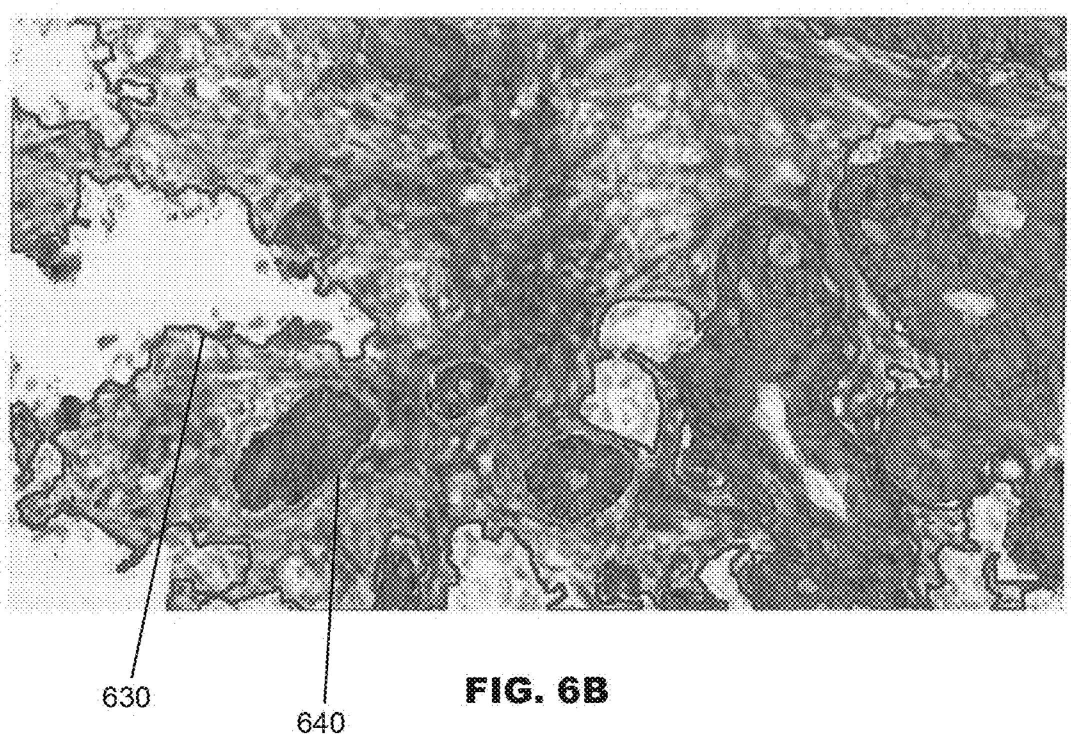
FIG. 6B sets forth an example of lower resolution polygon outlines (red, 630) for areas with positive fibroblast expression and exclusion regions (holes, 640) in cyan.

With reference to FIGS. 2 and 3, the present disclosure provides a computer-implemented method of analyzing and/or storing analysis results of biological objects having irregular shapes, including, for example, fibroblasts or macrophages in a database or other non-transitory memory. The method may include, for example, (a) running an image acquisition module 202 to generate or receive multi-channel image data, e.g. an acquired image of a biological sample stained with one or more stains (step 300); (b) running an image analysis module 205 to derive one or more metrics from features within the acquired image (step 310); (c) running a segmentation module 206 to segment the acquired image into a plurality of sub-regions (step 320); (d) running a representational object generation module 207 to generate polygons, center seeds, or other objects identifying the sub-regions (step 330); (c) running a labeling module 208 to associate the derived one or more metrics with the generated representational objects (step 340); and (f) storing the representational objects and associated metrics in a data base 209 (step 350). The skilled artisan will also appreciate that additional modules or databases may be incorporated into the workflow. For example, an image processing module may be run to apply certain filters to the acquired images or to identify certain histological and/or morphological structures within the tissue samples. In addition, a region of interest selection module may be utilized to select a particular portion of an image for analysis. Likewise, an unmixing module may be run to provide image channel images corresponding to a particular stain or biomarker.

Image Acquisition Module

In some embodiments, as an initial step, and with reference to FIG. 2, the digital pathology system 200 runs an image acquisition module 202 to capture images or image data of a biological sample having one or more stains (step 300). In some embodiments, the images received or acquired are RGB images or multispectral images (e.g. multiplex brightfield and/or darkfield images). In some embodiments, the images captured are stored in memory 201.

The images or image data (used interchangeably herein) may be acquired using the imaging apparatus 12, such as in real-time. In some embodiments, the images are acquired from a microscope or other instrument capable of capturing image data of a specimen-bearing microscope slide, as noted herein. In some embodiments, the images are acquired using a 2D scanner, such as one capable of scanning image tiles, or a line scanner capable of scanning the image in a line-by-line manner, such as the VENTANA DP 200 scanner. Alternatively, the images may be images that have been previously acquired (e.g. scanned) and stored in a memory 201 (or, for that matter, retrieved from a server via network 20).

The biological sample may be stained through application of one or more stains, and the resulting image or image data comprises signals corresponding to each of the one or more stains. As such, while the systems and methods described herein may estimate or normalize to a single stain, e.g. hematoxylin, there exists no limit on the number of stains within the biological sample. Indeed, the biological sample may have been stained in a multiplex assay for two or more stains, in addition to or including any counterstains.

As the skilled artisan will appreciate, a biological sample may be stained for different types of nuclei and/or cell membrane biomarkers. Methods for staining tissue structures and guidance in the choice of stains appropriate for various purposes are discussed, for example, in "Sambrook et al., Molecular Cloning: A Laboratory Manual, Cold Spring Harbor Laboratory Press (1989)" and "Ausubel et al., Current Protocols in Molecular Biology, Greene Publishing Associates and Wiley-Intersciences (1987)," the disclosures of which are incorporated herein by reference.

By way of one non-limiting example, in some embodiments the tissue sample is stained in an IHC assay for the presence of one or more biomarkers including a fibroblast activation protein (FAP). Over-expression of FAP in fibroblastic cell lines is believed to promote malignant behavior. It has been shown that stromal fibroblasts, which are an essential component of the tumor microenvironment and which have often been designated as cancer-associated fibroblasts (CAFs), can promote tumorigenesis and progression through multiple mechanisms, including proliferation, angiogenesis, invasion, survival and immune suppression. Without wishing to be bound by any particular theory, it is believed that cancer cells activate stromal fibroblasts and induce the expression of FAP, which in turn, affects the proliferation, invasion and migration of the cancer cells. It is believed that FAP is heavily expressed on reactive stromal fibroblasts in 90% of human epithelial carcinomas, including those of the breast, lung, colorectal, ovary, pancreas, and head-and-neck. Thus, the quantity of FAP most likely presents an important prognosis for the clinical behavior of tumors (and this is an example of one type of metrics that may be derived and later associated with a generated sub-region or representational object).

Chromogenic stains may comprise Hematoxylin, Eosin, Fast Red, or 3,3'-Diaminobenzidine (DAB). Of course, the skilled artisan will appreciate that any biological sample may also be stained with one or more fluorophores. In some embodiments, the tissue sample is stained with a primary stain (e.g. hematoxylin). In some embodiments, the tissue sample is stained in an IHC assay for a particular biomarker. The samples may also be stained with one or more fluorescent dyes.

A typical biological sample is processed in an automated staining/assay platform that applies a stain to the sample. There are a variety of commercial products on the market suitable for use as the staining/assay platform, one example being the Discovery™ product of Ventana Medical Systems, Inc. (Tucson, AZ). The camera platform may also include a bright field microscope, such as the VENTANA iScan HT or the VENTANA DP 200 scanners of Ventana Medical Systems, Inc., or any microscope having one or more objective lenses and a digital imager. Other techniques for capturing images at different wavelengths may be used. Further camera platforms suitable for imaging stained biological specimens are known in the art and commercially available from companies such as Zeiss, Canon, Applied Spectral Imaging, and others, and such platforms are readily adaptable for use in the system, methods and apparatus of this subject disclosure.

In some embodiments, the input images are masked such that only tissue regions are present in the images. In some embodiments, a tissue region mask is generated to mask non-tissue regions from tissue regions. In some embodiments, a tissue region mask may be created by identifying the tissue regions and automatically or semi-automatically (i.e., with minimal user input) excluding the background regions (e.g. regions of a whole slide image corresponding to glass with no sample, such as where there exists only white light from the imaging source). The skilled artisan will appreciate that in addition to masking non-tissue regions from tissue regions, the tissue masking module may also mask other areas of interest as needed, such as a portion of a tissue identified as belonging to a certain tissue type or belonging to a suspected tumor region. In some embodiments, a segmentation technique is used to generate the tissue region masked images by masking tissue regions from non-tissue regions in the input images. Suitable segmentation techniques are as such known from the prior art, (cf. Digital Image Processing, Third Edition, Rafael C. Gonzalez, Richard E. Woods, chapter 10, page 689 and Handbook of Medical Imaging, Processing and Analysis, Isaac N. Bankman Academic Press, 2000, chapter 2). In some embodiments, an image segmentation technique is utilized to distinguish between the digitized tissue data and the slide in the image, the tissue corresponding to the foreground and the slide corresponding to the background. In some embodiments, the component computes the Area of Interest (AOI) in a whole slide image in order to detect all tissue regions in the AOI while limiting the amount of background non-tissue area that is analyzed. A wide range of image segmentation techniques (e.g., HSV color-based image segmentation, Lab image segmentation, mean-shift color image segmentation, region growing, level set methods, fast marching methods, etc.) can be used to determine, for example, boundaries of the tissue data and non-tissue or background data. Based at least in part on the segmentation, the component can also generate a tissue foreground mask that can be used to identify those portions of the digitized slide data that correspond to the tissue data. Alternatively, the component can generate a background mask used to identify those portions of the digitized slide date that do not correspond to the tissue data.

This identification may be enabled by image analysis operations such as edge detection, etc. A tissue region mask may be used to remove the non-tissue background noise in the image, for example the non-tissue regions. In some embodiments, the generation of the tissue region mask comprises one or more of the following operations (but not limited to the following operations): computing the luminance of the low resolution analysis input image, producing a luminance image, applying a standard deviation filter to the luminance image, producing a filtered luminance image, and applying a threshold to filtered luminance image, such that pixels with a luminance above a given threshold are set to one, and pixels below the threshold are set to zero, producing the tissue region mask. Additional information and examples relating to the generation of tissue region masks is disclosed in PCT/EP/2015/062015, entitled "An Image Processing Method and System for Analyzing a Multi-Channel Image Obtained from a Biological Tissue Sample Being Stained by Multiple Stains," the disclosure of which is hereby incorporated by reference herein in its entirety.

Figure 13:
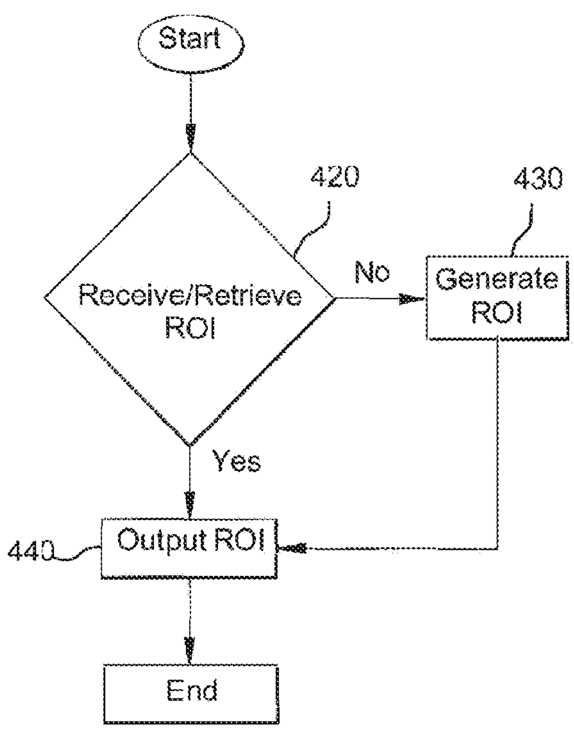
FIG. 13 provides a flow chart illustrating the steps of region selection, in accordance with some embodiments.

In some embodiments, a region of interest identification module may be used to select a portion of the biological sample for which an image or for which image data should be acquired, e.g. a region of interest having a large concentration of fibroblast cells. FIG. 13 provides a flow chart illustrating the steps of region selection, in accordance with some embodiments. In step 420, the region selection module receives an identified region of interest or field of view. In some embodiments, the region of interest is identified by a user of a system of the present disclosure, or another system communicatively coupled to a system of the present disclosure. Alternatively, and in other embodiments, the region selection module retrieves a location or identification of a region or interest from a storage/memory. In some embodiments, as shown in step 430, the region selection module automatically generates a field of view (FOV) or a region of interest (ROI), for example, via methods described in PCT/EP2015/062015, the disclosure of which is hereby incorporated by reference herein in its entirety. In some embodiments, the region of interest is automatically determined by the system based on some predetermined criteria or characteristics that are in or of the image (e.g. for a biological sample stained with more than two stains, identifying an area of the image that comprises just two stains). In step 440, the region selection module outputs the ROI.

Image Analysis Module

In some embodiments, certain metrics, e.g. FAP-positive area, FAP-positive intensity, are derived from features within the images received as input (step 300) (see FIG. 3). The derived metrics may be correlated with the sub-regions generated herein (steps 320, 330, and 340), and together the metrics (or averages, standard deviations, etc. thereof) and sub-region locations may be stored in a database (step 350) for later retrieval and/or downstream processing. The procedures and algorithms described herein may be adapted to derive metrics from and/or classify various types of cells or cell nuclei, including deriving metrics from fibroblasts and/or macrophages.

In some embodiments, the metrics are derived by detecting nuclei within the input image and/or by extracting features from the detected nuclei (such as from image patches surrounding the detected nuclei) and/or from cell membranes (depending, of course, on the biomarker(s) utilized within the input image). In other embodiments, metrics are derived by analyzing cell membrane staining, cell cytoplasm staining, and/or punctuate staining (e.g. to distinguish between membrane-staining areas and non-membrane staining areas). As used herein, the term "cytoplasmic staining" refers to a group of pixels arranged in a pattern bearing the morphological characteristics of a cytoplasmic region of a cell. As used herein, the term "membrane staining" refers to a group of pixels arranged in a pattern bearing the morphological characteristics of a cell membrane. As used herein, the term "punctate staining" refers to a group of pixels with strong localized intensity of staining appearing as spots/dots scattering on the membrane area of the cell. The skilled artisan will appreciate that the nucleus, cytoplasm and membrane of a cell have different characteristics and that differently stained tissue samples may reveal different biological features. Indeed, the skilled artisan will appreciate that certain cell surface receptors can have staining patterns localized to the membrane or localized to the cytoplasm. Thus, a "membrane" staining pattern is analytically distinct from a "cytoplasmic" staining pattern. Likewise, a "cytoplasmic" staining pattern and a "nuclear" staining pattern are analytically distinct. For example, stromal cells may be strongly stained by FAP, whereas tumor epithelial cells may be strongly stained by EpCAM, while cytokeratins may be stained by panCK. Thus, by utilizing different stains different cell types may be differentiated and distinguished during image analysis, and different metrics may be derived.

Methods of identifying and/or scoring nuclei, cell membranes, and cell cytoplasm in images of biological samples having one or more stains are described in U.S. Pat. No. 7,760,927 ("the '927 Patent"), the disclosure of which is hereby incorporated by reference herein in its entirety. For example, the '927 Patent describes an automated method for simultaneously identifying a plurality of pixels in an input image of a biological tissue stained with a biomarker, including considering a first color plane of a plurality of pixels in a foreground of the input image for simultaneous identification of cell cytoplasm and cell membrane pixels, wherein the input image has been processed to remove background portions of the input image and to remove counterstained components of the input image; determining a threshold level between cell cytoplasm and cell membrane pixels in the foreground of the digital image; and determining simultaneously with a selected pixel and its eight neighbors from the foreground if the selected pixel is a cell cytoplasm pixel, a cell membrane pixel or a transitional pixel in the digital image using the determined threshold level. The '927 Patent further describes that the step of determining simultaneously with a selected pixel and its eight neighbors includes: determining a square root of a product of the selected pixel with its eight neighboring pixels; comparing the product to the determined threshold level; incrementing a first counter for a cell membrane, a second counter for cell cytoplasm or a third counter for transitional pixel based on the comparison; determining whether the first counter, second counter or third counter exceeds a pre-determined maximum value, and if so, classifying the selected pixel based on a counter that exceeds the predetermined maximum value. In addition to scoring nuclei, the '927 Patent provides examples on scoring cytoplasm and membranes, such as based on computed cytoplasm pixel volume indexes, cytoplasm pixel median intensity, membrane pixel volume, and membrane pixel median intensity, respectively.

Additional methods of identifying and/or scoring membranes, nuclei, and other cellular features of interest are described in PCT Publication No. WO/2017/037180 ("the '180 Publication"), the disclosure of which is incorporated by reference herein in its entirety. The '180 Publication further describes methods of quantifying membrane staining of an analyte of interest in a biological sample where regions of membrane staining are intermixed with cytoplasmic staining and/or punctuate staining. To accomplish this, the '180 Publication describes a method of quantifying analyte staining of a biological compartment in a region in which the staining is intermixed with analyte staining of an analytically-distinct different biological compartment (e.g. (i) a region in which diffuse membrane staining is intermixed with cytoplasmic staining, or (ii) a region in which diffuse membrane staining is intermixed with punctate staining) by: (A) segmenting the digital image of the tissue or cytological sample into a plurality of distinct regions on the basis of analyte staining pattern, the plurality of regions comprising at least one compound staining region, i.e., a region of the image having analyte-positive staining in a first biological compartment intermixed with analyte-positive staining in at least a second biological compartment, wherein said first biological compartment and said at least a second biological compartment are analytically distinct; (B) separately from (A), identifying candidate biological compartments, i.e., pixel clusters in the digital image that correspond to at least the first biological compartment; (C) separately from (A) and (B), generating an analyte intensity map by segmenting clusters of pixels corresponding to analyte staining into a high intensity bin, a low intensity bin, and a background intensity bin; (D) identifying analytically relevant portions of each compound staining region by matching the candidate biological compartments within the compound staining region with an appropriate bin from the analyte intensity map; and (E) quantifying analyte staining in analytically relevant portions of the compound staining region. Pixels in any identified compartment can then be quantified such that the area of the compartment or staining intensity quantification may be determined. The '180 Publication also describes scoring membrane-specific expression levels.

In some embodiments, scoring is performed on classified nuclei, resulting in percent positivity metric or an H-score metric for a particular biomarker. By identifying nuclei, corresponding cells may be identified. In other embodiments, cells are scored by associating respective nuclei with a stained membrane around them. Based on the presence of a stained membrane surrounding the nuclei, a cell may be classified, e.g. as non-stained (no stained membrane found around the nucleus), partially stained (the nucleus of the cell is partially surrounded by the stained membrane), or completely stained (the nucleus is completely surrounded by a stained membrane).

In some embodiments, tumor nuclei are automatically identified by first identifying candidate nuclei and then automatically distinguishing between tumor nuclei and non-tumor nuclei. Numerous methods of identifying candidate nuclei in images of tissue are known in the art. For example, automatic candidate nucleus detection can be performed by applying a radial-symmetry-base method, a radial-symmetry-based method of Parvin et al., as described herein, such as on the Hematoxylin image channel or a biomarker image channel obtained using color deconvolution as described by Ruifrok et al, also described herein. In one exemplary embodiment, a radial symmetry based nuclei detection operation is used as described in commonly-assigned and co-pending patent application WO2014140085A1, the entirety of which is incorporated herein by reference. Other methods are discussed in US Patent Publication No. 2017/0140246, the disclosure of which is incorporated by reference herein.

After candidate nuclei are identified, they are further analyzed to distinguish tumor nuclei from other candidate nuclei. The other candidate nuclei may be further classified (for example, by identifying lymphocyte nuclei and stroma nuclei). In some embodiments, a learnt supervised classifier is applied to identify tumor nuclei. For example, the learnt supervised classifier is trained on nuclei features to identify tumor nuclei and then applied to classify the nucleus candidate in the test image as either a tumor nucleus or a non-tumor nucleus. Optionally, the learnt supervised classifier may be further trained to distinguish between different classes of non-tumor nuclei, such as lymphocyte nuclei and stromal nuclei. In some embodiments, the learnt supervised classifier used to identify tumor nuclei is a random forest classifier. For example, the random forest classifier may be trained by: (i) creating a training set of tumor and non-tumor nuclei, (ii) extracting features for each nucleus, and (iii) training the random forest classifier to distinguish between tumor nuclei and non-tumor nuclei based on the extracted features. The trained random forest classifier may then be applied to classify the nuclei in a test image into tumor nuclei and non-tumor nuclei. Optionally, the random forest classifier may be further trained to distinguish between different classes of non-tumor nuclei, such as lymphocyte nuclei and stromal nuclei.

In some embodiments, the images received as input are processed such as to detect nucleus centers (seeds) and/or to segment the nuclei. For example, instructions may be provided to detect nucleus centers based on radial-symmetry voting using techniques commonly known to those of ordinary skill in the art (see Parvin, Bahram, et al. "Iterative voting for inference of structural saliency and characterization of subcellular events." Image Processing, IEEE Transactions on 16.3 (2007): 615-623, the disclosure of which is incorporated by reference in its entirety herein). In some embodiments, nuclei are detected using radial symmetry to detect centers of nuclei and then the nuclei are classified based on the intensity of stains around the cell centers. For example, an image magnitude may be computed within an image and one or more votes at each pixel are accumulated by adding the summation of the magnitude within a selected region. Mean shift clustering may be used to find the local centers in the region, with the local centers representing actual nuclear locations. Nuclei detection based on radial symmetry voting is executed on color image intensity data and makes explicit use of the a priori domain knowledge that the nuclei are elliptical shaped blobs with varying sizes and eccentricities. To accomplish this, along with color intensities in the input image, image gradient information is also used in radial symmetry voting and combined with an adaptive segmentation process to precisely detect and localize the cell nuclei. A "gradient" as used herein is, for example, the intensity gradient of pixels calculated for a particular pixel by taking into consideration an intensity value gradient of a set of pixels surrounding said particular pixel. Each gradient may have a particular "orientation" relative to a coordinate system whose x- and y-axis are defined by two orthogonal edges of the digital image. For instance, nuclei seed detection involves defining a seed as a point which is assumed to lie inside a cell nucleus and serve as the starting point for localizing the cell nuclei. The first step is to detect seed points associated with each cell nuclei using a highly robust approach based on the radial symmetry to detect elliptical-shaped blobs, structures resembling cell nuclei. The radial symmetry approach operates on the gradient image using a kernel based voting procedure. A voting response matrix is created by processing each pixel that accumulates a vote through a voting kernel. The kernel is based on the gradient direction computed at that particular pixel and an expected range of minimum and maximum nucleus size and a voting kernel angle (typically in the range [$\pi/4$, $\pi/8$]). In the resulting voting space, local maxima locations that have a vote value higher than a predefined threshold value are saved out as seed points. Extraneous seeds may be discarded later during subsequent segmentation or classification processes.

Nuclei may be identified using other techniques known to those of ordinary skill in the art. For example, an image magnitude may be computed from a particular image channel of one of the H&E or IHC images, and each pixel around a specified magnitude may be assigned a number of votes that is based on a summation of the magnitude within a region around the pixel. Alternatively, a mean shift clustering operation may be performed to find the local centers within a voting image, which represents the actual location of the nucleus. In other embodiments, nuclear segmentation may be used to segment the entire nucleus based on the now-known centers of the nuclei via morphological operations and local thresholding. In yet other embodiments, model based segmentation may be utilized to detect nuclei (i.e. learning the shape model of the nuclei from a training data set and using that as the prior knowledge to segment the nuclei in the testing image).

In some embodiments, the nuclei are then subsequently segmented using thresholds individually computed for each nucleus. For example, Otsu's method may be used for segmentation in a region around an identified nucleus since it is believed that the pixel intensity in the nuclear regions varies. As will be appreciated by those of ordinary skill in the art, Otsu's method is used to determine an optimal threshold by minimizing the intra-class variance and is known to those of skill in the art. More specifically, Otsu's method is used to automatically perform clustering-based image thresholding or, the reduction of a gray level image to a binary image. The algorithm assumes that the image contains two classes of pixels following a bi-modal histogram (foreground pixels and background pixels). It then calculates the optimum threshold separating the two classes such that their combined spread (intra-class variance) is minimal, or equivalent (because the sum of pairwise squared distances is constant), so that their inter-class variance is maximal.

In some embodiments, the systems and methods further comprise automatically analyzing spectral and/or shape features of the identified nuclei in an image for identifying nuclei of non-tumor cells. For example, blobs may be identified in the first digital image in a first step. A "blob" as used herein can be, for example, a region of a digital image in which some properties, e.g. the intensity or grey value, are constant or vary within a prescribed range of values. All pixels in a blob can be considered in some sense to be similar to each other. For example, blobs may be identified using differential methods which are based on derivatives of a function of position on the digital image, and methods based on local extrema. A nuclear blob is a blob whose pixels and/or whose outline shape indicate that the blob was probably generated by a nucleus stained with the first stain. For example, the radial symmetry of a blob could be evaluated to determine if the blob should be identified as a nuclear blob or as any other structure, e.g. a staining artifact. For example, in case a blob has a lengthy shape and is not radially symmetric, said blob may not be identified as a nuclear blob but rather as a staining artifact. Depending on the embodiment, a blob identified to be a "nuclear blob" may represent a set of pixels which are identified as candidate nuclei, and which may be further analyzed for determining if said nuclear blob represents a nucleus. In some embodiments, any kind of nuclear blob is directly used as an "identified nucleus." In some embodiments, filtering operations are applied on the identified nuclei or nuclear blobs for identifying nuclei which do not belong to biomarker-positive tumor cells and for removing said identified non-tumor nuclei from the list of already identified nuclei or not adding said nuclei to the list of identified nuclei from the beginning. For example, additional spectral and/or shape features of the identified nuclear blob may be analyzed to determine if the nucleus or nuclear blob is a nucleus of a tumor cell or not. For example, the nucleus of a lymphocyte is larger than the nucleus of other tissue cell, e.g. of a lung cell. In case the tumor cells are derived from a lung tissue, nuclei of lymphocytes are identified by identifying all nuclear blobs of a minimum size or diameter which is significantly larger than the average size or diameter of a normal lung cell nucleus. The identified nuclear blobs relating to the nuclei of lymphocytes may be removed (i.e., "filtered out from") the set of already identified nuclei. By filtering out the nuclei of non-tumor cells, the accuracy of the method may be increased. Depending on the biomarker, also non-tumor cells may express the biomarker to a certain extent and may therefore produce an intensity signal in the first digital image which does not stem from a tumor cell. By identifying and filtering out nuclei which do not belong to tumor cells from the totality of the already identified nuclei, the accuracy of identifying biomarker-positive tumor cells may be increased. These and other methods are described in US Patent Publication 2017/0103521, the disclosure of which is incorporated by reference herein in its entirety. In some embodiments, once the seeds are detected, a locally adaptive thresholding method may be used, and blobs around the detected centers are created. In some embodiments, other methods may also be incorporated, such as marker based watershed algorithms can also be used to identify the nuclei blobs around the detected nuclei centers. These and other methods are described in co-pending application PCT/EP2016/051906, published as WO2016/120442, the disclosure of which is incorporated by reference herein in its entirety.

The system can use at least one image characteristic metric and at least one morphology metric to determine whether a feature within an image corresponds to a structure of interest (collectively "feature metrics"). Image characteristic metrics (derived from features within an image) can include, for example, color, color balance, intensity, or the like. Morphology metrics (derived from features within an image) can include, for example, feature size, feature color, feature orientation, feature shape, relation or distance between features (e.g., adjacent features), relation or distance of a feature relative to another anatomical structure, or the like. Image characteristic metrics, morphology metrics, and other metrics can be used to train a classifier as described herein. Specific examples of metrics derived from image features are set forth below:

(A) Metrics Derived from Morphology Features

A "morphology feature" as used herein is, for example, a feature being indicative of the shape or dimensions of a nucleus. Without wishing to be bound by any particular theory, it is believed that morphological features provide some vital information about the size and shape of a cell or its nucleus. For example, a morphology feature may be computed by applying various image analysis algorithms on pixels contained in or surrounding a nuclear blob or seed. In some embodiments, the morphology features include area, minor, and major axis lengths, perimeter, radius, solidity, etc.

(B) Metrics Derived from Appearance Features

An "appearance feature" as used herein is, for example, a feature having been computed for a particular nucleus by comparing pixel intensity values of pixels contained in or surrounding a nuclear blob or seed used for identifying the nucleus, whereby the compared pixel intensities are derived from different image channels (e.g. a background channel, a channel for the staining of a biomarker, etc.). In some embodiments, the metrics derived from appearance features are computed from percentile values (e.g. the 10th, 50th, and 95th percentile values) of pixel intensities and of gradient magnitudes computed from different image channels. For example, at first, a number P of X-percentile values (X=10, 50, 95) of pixel values of each of a plurality IC of image channels (e.g. three channels: HTX, DAB, luminance)

within a nuclear blob representing the nucleus of interest are identified. Computing appearance feature metrics may be advantageous since the derived metrics may describe the properties of the nuclear regions as well as describe the membrane region around the nuclei.

(C) Metrics Derived from Background Features

A "background feature" is, for example, a feature being indicative of the appearance and/or stain presence in cytoplasm and cell membrane features of the cell comprising the nucleus for which the background feature was extracted from the image. A background feature and a corresponding metrics can be computed for a nucleus and a corresponding cell depicted in a digital image e.g. by identifying a nuclear blob or seed representing the nucleus; analyzing a pixel area (e.g. a ribbon of 20 pixels—about 9 microns—thickness around the nuclear blob boundary) directly adjacent to the identified set of cells are computed in, therefore capturing appearance and stain presence in cytoplasm and membrane of the cell with this nucleus together with areas directly adjacent to the cell. These metrics are similar to the nuclear appearance features but are computed in a ribbon of about 20 pixels (about 9 microns) thickness around each nucleus boundary, therefore capturing the appearance and stain presence in the cytoplasm and membrane of the cell having the identified nucleus together with areas directly adjacent to the cell. Without wishing to be bound by any particular theory, the ribbon size is selected because it is believed that it captures a sufficient amount of background tissue area around the nuclei that can be used to provide useful information for nuclei discrimination. These features are similar to those disclosed by "J. Kong, et al., "A comprehensive framework for classification of nuclei in digital microscopy imaging: An application to diffuse gliomas," in ISBI, 2011, pp. 2128-2131" the disclosure of which is incorporated by reference in its entirety herein. It is believed that these features may be used to determine whether the surrounding tissue is stroma or epithelium (such as in H&E stained tissue samples). Without wishing to be bound by any particular theory, it is believed that these background features also capture membrane staining patterns, which are useful when the tissue samples are stained with appropriate membrane staining agents.

(D) Metrics Derived from Color.

In some embodiments, metrics derived from color include color ratios, R/(R+G+B). or color principal components. In other embodiments, metrics derived from color include local statistics of each of the colors (mean/median/variance/std dev) and/or color intensity correlations in a local image window.

(E) Metrics Derived from Intensity Features

The group of adjacent cells with certain specific property values is set up between the dark and the white shades of grey colored cells represented in a histopathological slide image. The correlation of the color feature defines an instance of the size class, thus this way the intensity of these colored cells determines the affected cell from its surrounding cluster of dark cells. Examples of texture features are described in PCT Publication No. WO/2016/075095, the disclosure of which is incorporated by reference herein in its entirety.

(F) Spatial Features

In some embodiments, spatial features include a local density of cells; average distance between two adjacent detected cells; and/or distance from a cell to a segmented region.

(G) Metrics Derived from Nuclear Features

The skilled artisan will also appreciate that metrics may also be derived from nuclear features. The computation of such nuclear features is described by Xing et al. "Robust Nucleus/Cell Detection and Segmentation in Digital Pathology and Microscopy Images: A Comprehensive Review," IEEE Rev Biomed Eng 9, 234-263, January 2016, the disclosure of which is hereby incorporated by reference herein in its entirety. Of course, other features, as known to those of ordinary skill in the art, may be considered and used as the basis for computation of features.

After feature metrics are derived, the feature may be used alone or in conjunction with training data (e.g. during training, example cells are presented together with a ground truth identification provided by an expert observer according to procedures known to those of ordinary skill in the art) to classify nuclei or cells. In some embodiments, the system can include a classifier that was trained based at least in part on a set of training or reference slides for each biomarker. The skilled artisan will appreciate that different sets of slides can be used to train a classifier for each biomarker. Accordingly, for a single biomarker, a single classifier is obtained after training. The skilled artisan will also appreciate that since there is variability between the image data obtained from different biomarkers, a different classifier can be trained for each different biomarker so as to ensure better performance on unseen test data, where the biomarker type of the test data will be known. The trained classifier can be selected based at least in part on how best to handle training data variability, for example, in tissue type, staining protocol, and other features of interest, for slide interpretation.

In some embodiments, the classification module is a Support Vector Machine ("SVM"). In general, a SVM is a classification technique, which is based on statistical learning theory where a nonlinear input data set is converted into a high dimensional linear feature space via kernels for the non-linear case. Without wishing to be bound by any particular theory, it is believed that support vector machines project a set of training data, E, that represents two different classes into a high-dimensional space by means of a kernel function, K. In this transformed data space, nonlinear data are transformed so that a flat line can be generated (a discriminating hyperplane) to separate the classes so as to maximize the class separation. Testing data are then projected into the high-dimensional space via K, and the test data are classified on the basis of where they fall with respect to the hyperplane. The kernel function K defines the method in which data are projected into the high-dimensional space.

In other embodiments, classification is performed using an AdaBoost algorithm. The AdaBoost is an adaptive algorithm which combines a number of weak classifiers to generate a strong classifier. Image pixels identified by a pathologist during the training stage (e.g. those having a particular stain or belonging to a particular tissue type) are used to generate probability density functions for each of the individual texture features Φj, for j∈{1, . . . , K} which are considered as weak classifiers. Bayes Theorem is then used to generate likelihood scenes Lj=(Cj, 1j∈{1, . . . , K}) for each Φj which constitute the weak learners. These are combined by the AdaBoost algorithm into a strong classifier Πj=ΣTi=1αjilji where for every pixel cj∈Cj, Πj (cj) is the combined likelihood that pixel cj belongs to class ωT, where αji is the weight determined during training for feature Φi, and T is the number of iterations.

In some embodiments, derived stain intensity values, counts of specific nuclei, or other classification results may be used to determine various marker expression scores (used interchangeably with the term "expression score" herein), such as percent positivity or an H-Score (i.e. from the classified features, expression scores may be calculated). Methods for scoring are described in further detail in commonly-assigned and co-pending applications WO/2014/102130A1 "Image analysis for breast cancer prognosis" filed Dec. 19, 2013, and WO/2014/140085A1 "Tissue object-based machine learning system for automated scoring of digital whole slides," filed Mar. 12, 2104, the contents of each are hereby incorporated by reference in their entirety herein. For example, based at least in part on the number of biomarker-positive tumor cells/biomarker-positive non-tumor cells, a score (e.g., a whole-slide score) can be determined. In some embodiments, for each detected nuclear blob, average blob intensity, color and geometric features, such as area and shape of the detected nuclear blob may be computed, and the nuclear blobs are classified into tumor nuclei and nuclei of non-tumor cells. The number of identified nuclei output corresponds to the total number of biomarker-positive tumor cells detected in the FOV, as evidenced by the number of tumor nuclei counted.

In some embodiments, and again in the context of staining with FAP, the feature metrics are derived, and a classifier is trained such that a percentage (e.g. a percent positivity expression score) of FAP positive or negative cells may be elucidated, e.g. positively or negatively stained stromal cells. In some embodiments, a score of 0 may be assigned to a stained area with ≤10% of the tumor cells, 1 for an area with >11% to ≤25% of tumor cells, 2 for >26% to ≤50% tumor cells, and 3 for >51% tumor cells. For the staining intensity, a score of 0 may be assigned for absent/weak staining (negative control), 1 for a weak staining obviously stronger than the negative control level, 2 for moderately intense staining, and 3 for intense staining. In some embodiments, a final score of ≥3 may be recognized to indicate positive expression of FAP.

Segmentation Module

The mid-resolution analysis approach employs segmentation algorithms to generate the sub-regions within the input images, the sub-regions defined to capture biologically meaningful regions of interest. Following the derivation of metrics from the input images (step 310) with the image analysis module 205, a segmentation generation module 206 is utilized to segment the input image into a plurality of sub-regions (step 320).

In some embodiments, segmentation is performed on a single channel image, e.g. a "purple" channel in an unmixed FAP image. Methods of unmixing are known to those of ordinary skill in the art (e.g. linear unmixing is described, for example, in 'Zimmermann "Spectral Imaging and Linear Unmixing in Light Microscopy" Adv Biochem Engin/Biotechnol (2005) 95:245-265' and in in C. L. Lawson and R. J. Hanson, "Solving least squares Problems," Prentice Hall, 1974, Chapter 23, p. 161,' the disclosures of which are incorporated herein by reference in their entirety). Other methods of unmixing are disclosed herein. See also Ruifok et. al., Quantification of histochemical staining by color deconvolution," Anal Quant Cytol Histol. 2001 August; 23(4):291-9, the disclosure of which is hereby incorporated by reference herein in its entirety.

In some embodiments, the sub-regions generated capture information in an area of the input image having either a pre-determined size or a size within a range as set forth within an image processing algorithm (e.g. a parameter of a SLIC superpixel generation algorithm as described herein).

Figure 7:
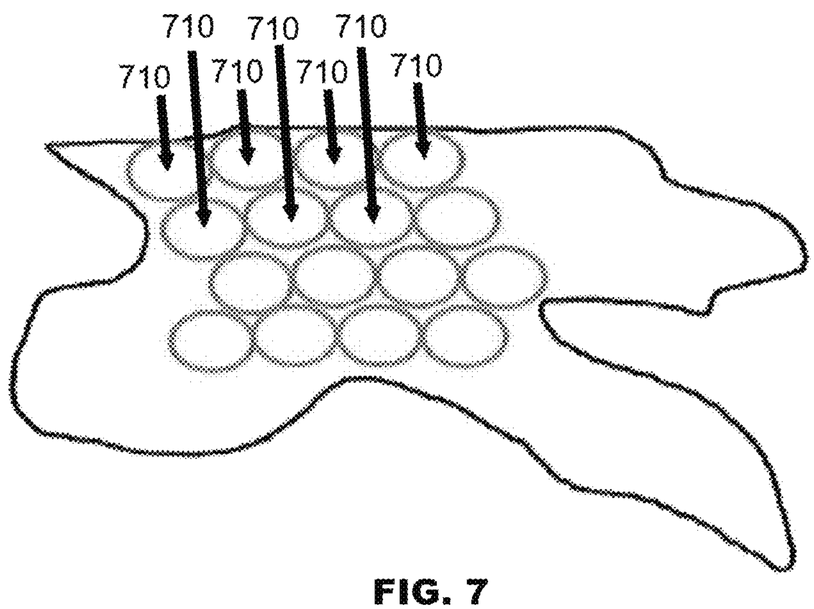
FIG. 7 illustrates sub-regions (710) having a simple shape (e.g. circle) which may be associated with image data using the mid-resolution approach described herein.

In some embodiments, the input image is segmented into sub-regions having a predefined shape, size, area, and/or spacing. For example, the sub-regions (710) may be ovals, circles, squares, rectangles, etc., such as depicted in FIG. 7. In some embodiments, the oval, circular, square, or rectangular sub-regions may have a size ranging from between 50 pixels to about 100 pixels, or some other size such that groups of pixels are selected having similar properties or characteristics (e.g. color, brightness, and/or texture). In some embodiments, the sub-regions are non-overlapping, and may be generated via a sampling grid. As used herein, the term "sampling grid" relates to a network of horizontal and perpendicular lines which are uniformly spaced and superimposed onto an image, ultimately used for locating points non-overlapping points within an image. In some embodiments, any number of adjacent positions established by the horizontal and perpendicular lines may be used to define an image segment. In some embodiments, the sub-regions are distributed across the image in a manner that captures a representative sample of relevant regions for analysis, e.g. areas where irregularly shaped cells are a predominant feature.

In other embodiments, the input image is segmented by applying a series of algorithms to the image, including global thresholding filters, local adaptive thresholding filters, morphological operations, and watershed transformations. The filters may be run sequentially or in any order deemed necessary by those of ordinary skill in the art. Of course, any filter may be applied iteratively until the desired outcome is achieved. In some embodiments, a first filter is applied to the input image to remove regions that are unlikely to have nuclei, such as removing those image regions that are white (corresponding to regions in the tissue samples that are unstained or nearly unstained). In some embodiments, this is achieved by applying a global thresholding filter. In some embodiments, the global thresholding is based on a median and/or standard deviation computed on a first principal component channel, e.g. similar to a gray scale channel. By obtaining the global threshold, it is believed that any white image regions, which are representative of unstained or nearly unstained regions where nuclei are likely not present, can be discarded. Filters are then applied to the image to selectively remove artifacts, e.g. small blobs, small discontinuities, other small objects, and/or to fill holes. In some embodiments, morphological operators are applied to remove artifacts and/or fill holes. In some embodiments, a distance-based watershed is applied, based on a binary image introduced as input (e.g. a binary image resulting from prior filtering steps).

In some embodiments, the input image is segmented into superpixels. It is believed that a superpixels algorithm partitions an image into a number of segments (group of pixels) that represent perceptually meaningful entities. Each superpixel is obtained by a low-level grouping process and has a perceptually consistent unit, i.e., all pixels in a biological object contained in a superpixel are as uniform as possible in staining presence (e.g. pixels present in the superpixel are of a particular type of stain), staining intensity (e.g. pixels have a certain relative intensity value or range of values), and texture (e.g. pixels have a particular spatial arrangement of color or intensities). The local analysis result of each superpixel can be stored and reported to represent the analysis results on digital pathology images.

A superpixel is a collection of pixels with similar characteristics, such as color, brightness, and texture. An image can be composed of a certain number of superpixels that contain multiple combination characteristics of the pixels and can preserve the edge information of the original image. Compared with a single pixel, a superpixel contains rich characteristic information and can greatly reduce image post-processing complexity and significantly increase the speed of image segmentation. Superpixels are also useful for estimating probabilities and making decisions with small neighborhood models.

Superpixel algorithms are methods that group pixels into meaningful atomic regions of similar size. Without wishing to be bound by any particular theory, it is believed that superpixels are powerful because they often fall on important boundaries within the image, and tend to take on abnormal or unique shapes when they contain salient object features. Consistent with the desire to obtain and store information at a medium resolution analysis, superpixels are located between pixel- and object-level: they carry more information than pixels by representing perceptually meaningful pixel groups, while not comprehensively representing image objects. Superpixels can be understood as a form of image segmentation, that over-segment the image in a short computing time. The outlines of superpixels have shown to adhere well to natural image boundaries, as most structures in the image are conserved. With image features being computed for each superpixel rather than each pixel, subsequent processing tasks are reduced in complexity and computing time. Thus, superpixels are considered useful as a preprocessing step for analyses at object level such as image segmentation.

Without wishing to be bound by any particular theory, it is believed that superpixels over-segment an image by forming compact and uniform groups of pixels that have similar characteristics in e.g., color or geometry. In the past, multiple superpixel approaches have been developed. They can be classified into (i) graph-based and (ii) gradient-ascent-based approaches. In a graph-based approach, each pixel is considered a node in a graph. An edge weight is defined between all pairs of nodes that is proportional to their similarity. Then, a cost function defined on the graph is formulated and minimized, in order to extract superpixel segments. In a gradient-ascent-based approach, pixels are iteratively mapped to a feature space to delineate denser regions that represent clusters. Each iteration refines each cluster to obtain a better segmentation until convergence.

Many superpixel algorithms have been developed, including normalized cuts, agglomerative clustering, quick shift and Turbopixel algorithms. The normalized cuts algorithm recursively partitions a graph of all pixels in the image using contour and texture cues, globally minimizing a cost function defined on the edges at the partition boundaries. It produces very regular, visually pleasing superpixels (see Jianbo Shi and Jitendra Malik. Normalized cuts and image segmentation, IEEE Transactions on Pattern Analysis and Machine Intelligence, (PAMI), 22(8):888-905, August 2000, the disclosure of which is incorporated by reference herein in its entirety). Alastair Moore, Simon Prince, Jonathan Warrell, Umar Mohammed, and Graham Jones. Superpixel Lattices. IEEE Computer Vision and Pattern Recognition (CVPR), 2008, describe a method to generate superpixels that conform to a grid by finding optimal paths, or scams, that split the image into smaller vertical or horizontal regions. Optimal paths are found using a graph cuts method (sec, Shai Avidan and Ariel Shamir. Seam carving for content-aware image resizing. ACM Transactions on Graphics (SIGGRAPH), 26(3), 2007, the disclosure of which are hereby incorporated by reference herein). Quick shift (see A. Vedaldi and S. Soatto). Quick shift and kernel methods for mode seeking. In European Conference on Computer Vision (ECCV), 2008, the disclosure of which is hereby incorporated by reference herein) uses a mode-seeking segmentation scheme. It initializes the segmentation using a medoid shift procedure. It then moves each point in the feature space to the nearest neighbor that increases the Parzen density estimate. The Turbopixel method progressively dilates a set of seed locations using level-set based geometric flow (see A. Levinshtein, A. Stere, K. Kutulakos, D. Fleet, S. Dickinson, and K. Siddiqi). Turbopixels: Fast superpixels using geometric flows. IEEE Transactions on Pattern Analysis and Machine Intelligence (PAMI), 2009, the disclosure of which is incorporated by reference herein). The geometric flow relies on local image gradients, aiming to regularly distribute superpixels on the image plane. Unlike other methods, the Turbopixel superpixels are constrained to have uniform size, compactness, and boundary adherence. Yet other methods of generating superpixels are described by Radhakrishna Achanta, "SLIC Superpixels Compared to State-of-the-art," Journal of Latex Class Files, Vol. 6, No. 1, December 2011, the disclosure of which is incorporated by herein in its entirety).

A superpixel algorithm called simple linear iterative clustering (SLIC) has been introduced, which, compared to the state-of-the-art superpixel methods, is superior for both boundary adherence and efficiency. The SLIC has two steps. Firstly, it generates superpixels by grouping pixels with a local k-means clustering (KMC) method, where the distance is measured as the Euclidean distance integrated with the data and spatial distances. Secondly, a connected components algorithm (CCA) is used to remove the generated small isolated regions by merging them into the nearest large superpixels.

K-means clustering aims to partition n observations into k clusters in which each observation belongs to the cluster with the nearest mean, serving as a prototype of the cluster. Connected component labeling works by scanning an image, pixel-by-pixel (from top to bottom and left to right) in order to identify connected pixel regions, i.e. regions of adjacent pixels which share the same set of intensity values V. (For a binary image $V=\{1\}$; however, in a gray level image V will take on a range of values, for example: $V=\{51, 52, 53, \ldots, 77, 78, 79, 80\}$.) Connected component labeling works on binary or gray level images and different measures of connectivity are possible. However, for the following we assume binary input images and 8-connectivity. The connected components labeling operator scans the image by moving along a row until it comes to a point p (where p denotes the pixel to be labeled at any stage in the scanning process) for which $V=\{1\}$. When this is true, it examines the four neighbors of p which have already been encountered in the scan (i.e. the neighbors (i) to the left of p, (ii) above it, and (iii and iv) the two upper diagonal terms). Based on this information, the labeling of p occurs as follows: If all four neighbors are 0, assign a new label to p, else if only one neighbor has $V=\{1\}$, assign its label to p, else if more than one of the neighbors have $V=\{1\}$, assign one of the labels to p and make a note of the equivalences.

After completing the scan, the equivalent label pairs are sorted into equivalence classes and a unique label is assigned to each class. As a final step, a second scan is made through the image, during which each label is replaced by the label assigned to its equivalence classes. For display, the labels might be different gray levels or colors.

SLIC is an adaptation of k-means for superpixel generation, with two important distinctions: (i) the number of distance calculations in the optimization is dramatically reduced by limiting the search space to a region proportional to the superpixel size (this is believed to reduce the complexity to be linear in the number of pixels—and independent of the number of superpixels k); and (ii) a weighted distance measure combines color and spatial proximity while simultaneously providing control over the size and compactness of the superpixels. (See Achanta, et al., "SLIC Superpixels Compared to State-of-the-Art Superpixel Methods," IEEE Transactions on Pattern Analysis and Machine Intelligence, Vol. 34, No. 11, November 2012, the disclosure of which is hereby incorporated by reference in its entirety herein).

SLIC considers image pixels in a 5D space, defined by the L*a*b values of the CIELAB color space as well as their x and y coordinates. Pixels in the 5D space are clustered based on an adapted k-means clustering integrating color similarity and proximity in the image plane. The clustering is based on a distance measure D that measures color similarity in L*a*b space (dc) and pixel proximity in x, y space (ds). The latter is normalized by a grid interval (S) that defines the square root of the total number of image pixels divided by the number of superpixels (k). The compactness and regularity of the superpixels is controlled with the constant m. This parameter functions as a weighting criteria between the spatial distance (dc) and the spectral distance (ds). A larger m, increases the weight of spatial proximity, which leads to more compact superpixels with boundaries adhering less to spectral outlines in the image.

$$D=\sqrt{\left(\frac{d_s}{m}\right)^2+\left(\frac{d_s}{S}\right)^2} \qquad \text{(Eq. 1)}$$

The SLIC algorithm may be applied as follows. Let $N_p$ be the number of pixels in a given image (or portion or region of interest thereof) and k the number of superpixels to generate. Next, the main steps of the SLIC algorithm are as follows:

(1) Initialize cluster centers. Set k initial cluster centers on a regular grid spaced $S=\sqrt{N_p/k}$ pixels apart, and then move these cluster centers to the positions with the lowest gradients in a 3×3 neighborhood. Without wishing to be bound by any particular theory, it is believed that is done to avoid centering a superpixel on an edge, and to reduce the chance of seeding a superpixel with a noisy pixel.

(2) Assign pixels. Designate each pixel to a closest cluster center in a local search space by local KMC.

(3) Update cluster centers. Set each cluster center as the mean of all pixels in the corresponding cluster.

(4) Repeat steps (2)-(3) until the clusters do not change or another given criterion is met.

(5) Post-processing. The CCA is used to reassign isolated regions to nearby superpixels if the size of the isolated regions is smaller than a minimum size $S_{min}$.

A local KMC is applied in step (2) of the SLIC method, where each pixel is associated with the closest cluster center whose search area covers its location. In conventional KMC, the search area of each cluster center is the whole image, and then the distances are calculated from each cluster center to every pixel in the image. In local KMC, however, the search space of a cluster center is limited to a local 2S×2S square region. Therefore, the SLIC only computes distances from each cluster center to pixels within its searching area.

In local KMC, Euclidean distance is used in the clustering. Let zi be the data of the i-th cluster center with its spatial position as $(x_i, y_i)$. Let $z_j$ be the intensity of a pixel within the search area of the center. Then, the integrated distance between this pixel and the center is:

$$D_I=\sqrt{(d_f/m)^2+(d_s/S)^2} \qquad \text{(Eq. 2)}$$

where $d_f=|z_i-z_j|$ and $d_s=\sqrt{(x_i-x_j)^2+(y_i-y_j)^2}$ are the intensity and spatial distances between the pixel and the center, respectively, and m is a regularization parameter that weights the relative contribution of $d_f$ and $d_s$ to the integrated distance $D_I$. A larger m indicates that $d_s$ is more significant than $d_f$. An equivalent integrated distance $D_I$ directly describing the contribution of the two distances can be given by:

$$D_I=\sqrt{w(d_f/N_f)^2+(1-w)(d_s/S)^2} \qquad \text{(Eq. 3)}$$

where $N_f$ is the mean intensity of the whole image, $w\in[0,1]$ is a regularization parameter. In this context, w and (1−w) are the ratios of the normalized intensity and spatial distances in $D_I$, respectively.

In some embodiments, the parameter k of the SLIC algorithm specifies the number of approximately equally sized superpixels. In some embodiments, the compactness parameter m can be set to control the trade-off between superpixels' homogeneity and boundary adherence. Without wishing to be bound by any particular theory, it is believed that by varying the compactness parameter, regular-shaped superpixels may be generated in untextured regions and highly irregular superpixels may be generated in textured regions. Again, without wishing to be bound by any particular theory, it is believed that the parameter m also allows for the weighting of the relative importance between color similarity and spatial proximity. When m is large, spatial proximity is more important and the resulting superpixels are more compact (i.e. they have a lower area to perimeter ratio). When m is small, the resulting superpixels adhere more tightly to image boundaries, but have less regular size and shape.

In some embodiments, both superpixel size and compactness parameters are adjusted. In some embodiments, a superpixel size ranging from between about 40 pixels and about 400 pixels is used. In other embodiments, a superpixel size ranging from between about 60 pixels and about 300 pixels is used. In yet other embodiments, a superpixel size ranging from between about 70 pixels and about 250 pixels is used. In yet further embodiments, a superpixel size ranging from between about 80 pixels and about 200 pixels is used.

In some embodiments, the compactness parameter ranges from about 10 to about 100. In other embodiments, the compactness parameter ranges from about 20 to about 90. In other embodiments, the compactness parameter ranges from about 40 to about 80. In other embodiments, the compactness parameter ranges from about 50 to about 80.

Figure 8A:
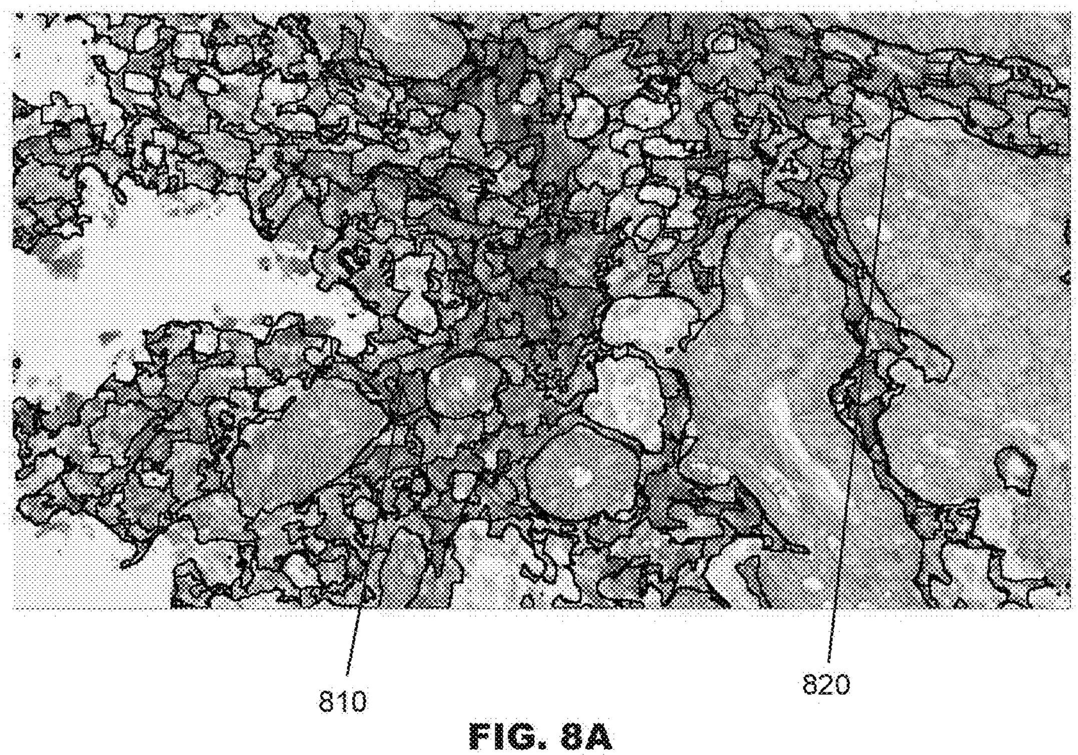
FIG. 8A sets forth an example of superpixels generated using SLIC in the fibroblast regions on an IHC image.
Figure 8B:
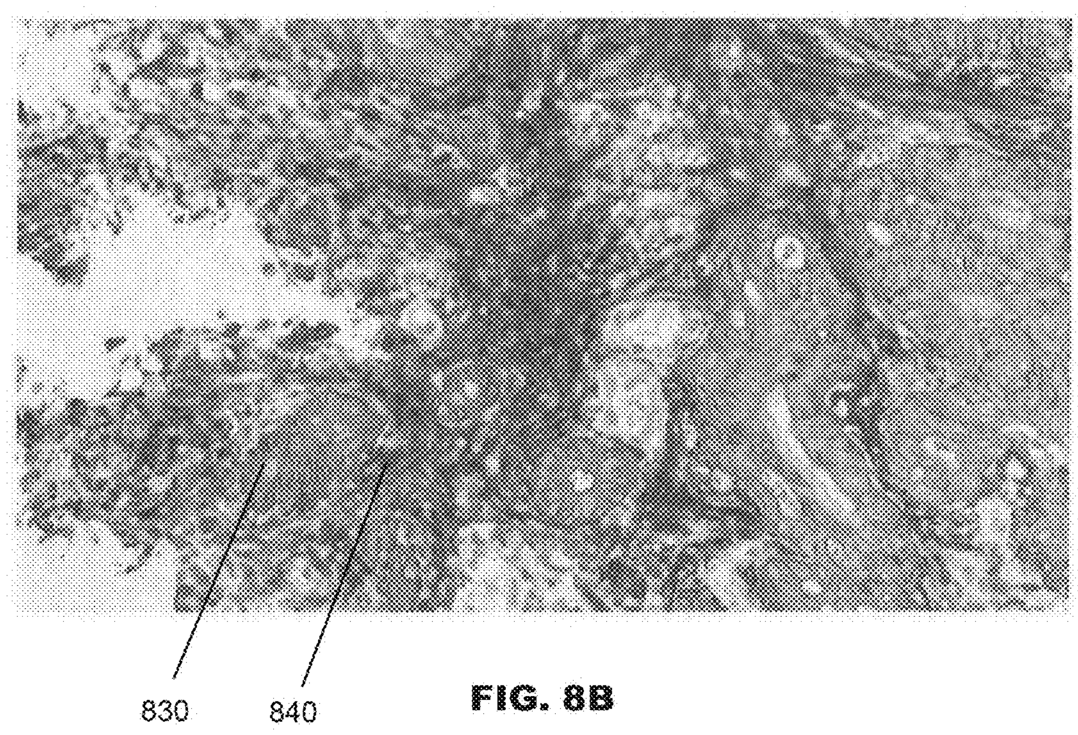
FIG. 8B provides an original IHC image at high magnification, where tumor cells (830) stained in yellow and fibroblasts (840) are stained in purple.
Figure 8C:
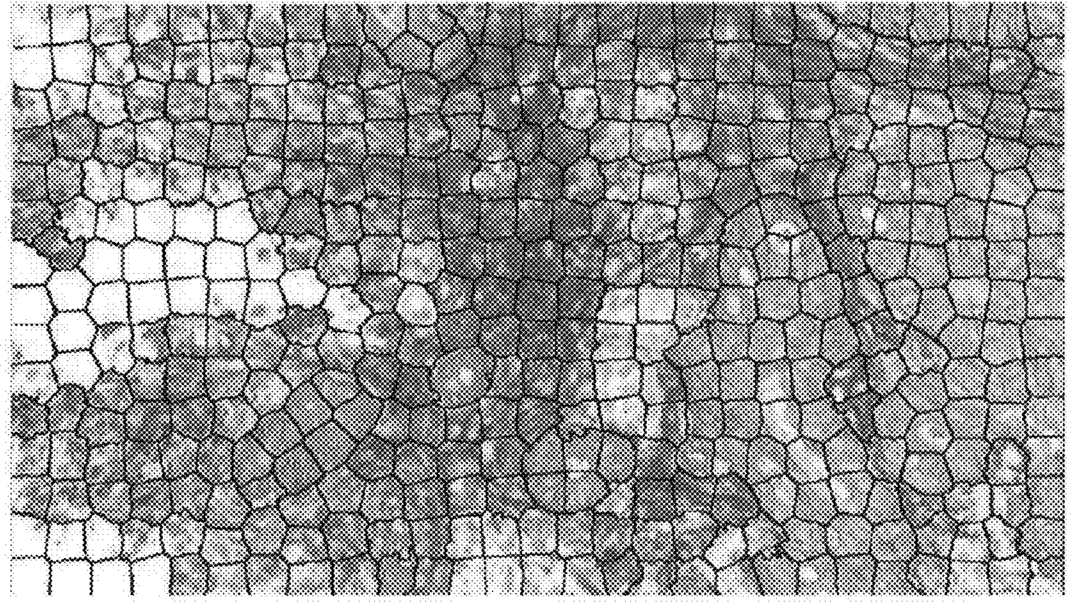
FIG. 8C illustrates an initial shape of superpixels, which appear similar to squares before a regularization parameter is adjusted, in accordance with some embodiments.
Figure 8D:
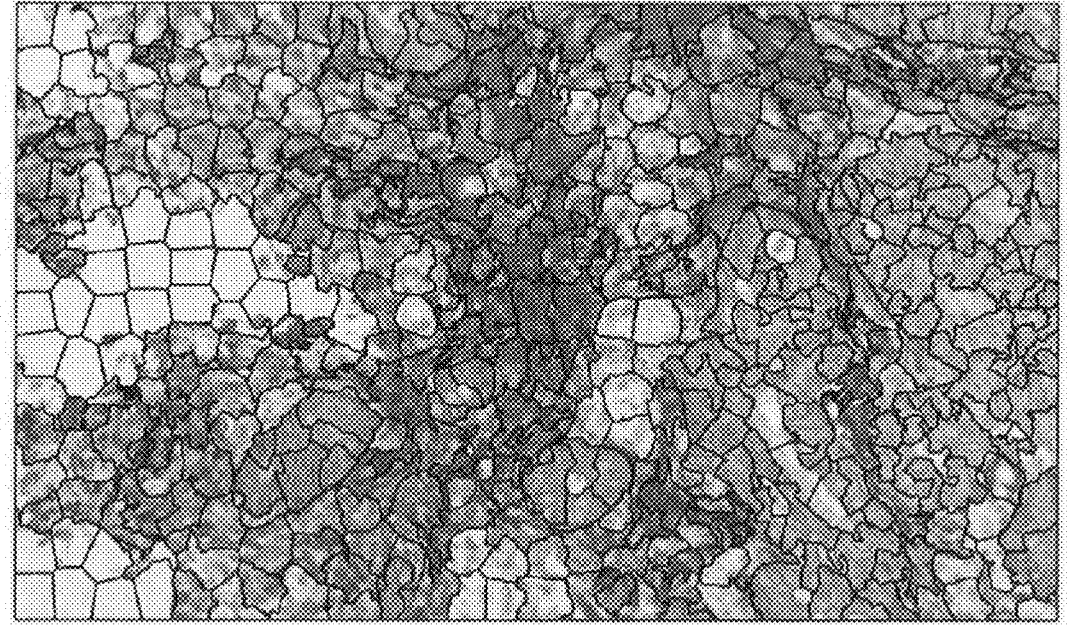
FIG. 8D illustrates a final representation of superpixels where the regularization parameter in the SLIC algorithm was adjusted, in accordance with some embodiments.

FIG. 8A illustrates an example of superpixels generated using SLIC as noted herein, where the superpixels are segmented to be appropriate for localized characteristics of the regions of interest without overlapping, and have no gaps among them. Moreover, each superpixel sub-region has a specific final shape depending on its local intensity (810) and direction (820) of the presence of biomarker expression. Hence, superpixels are perceptually meaningful for such biological structures of interest. FIGS. 8B, 8C, and 8D show an original IHC image at high magnification, the initialization of a superpixel generation process, and the final superpixels with local homogeneity, respectively, and where the regularity of their shape has been adjusted by a technical parameter of the SLIC algorithm, as noted above.

Representational Object Generation Module

Figure 9A:
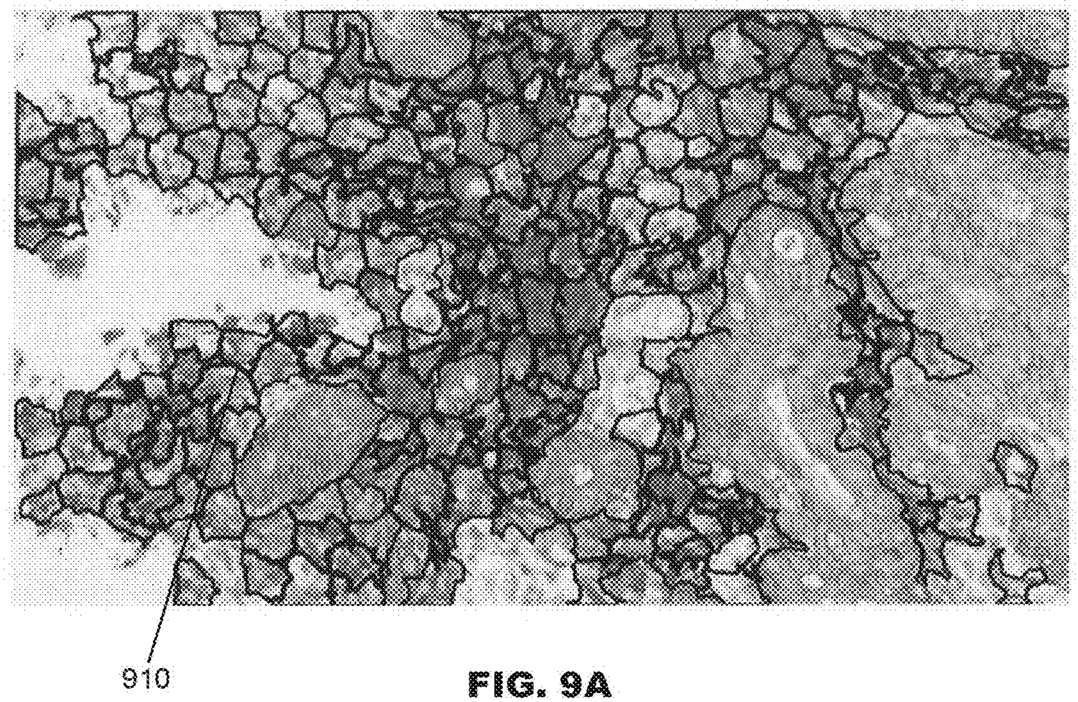
FIG. 9A illustrates polygon outlines (black, 910) of the sub-regions (here, superpixels) belonging to the regions of interest (fibroblast regions), in accordance with some embodiments.
Figure 9B:
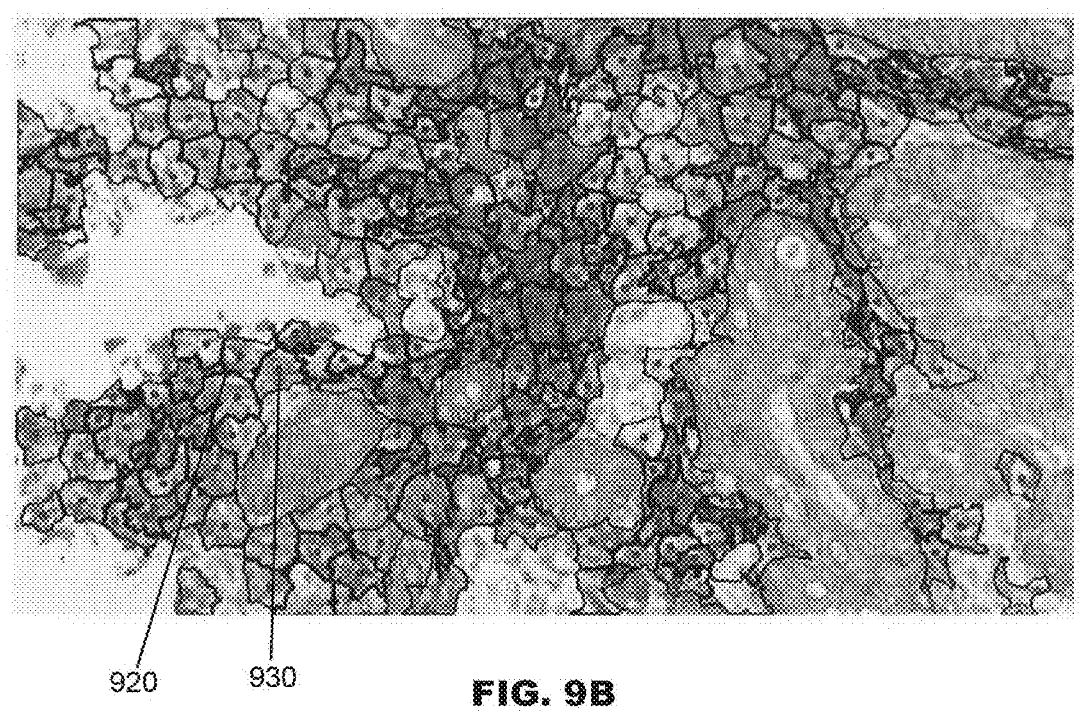
FIG. 9B sets forth polygon outlines (black, 920) and center seeds (green dots, 930) for the sub-regions (superpixels) belonging to the biological objects of interest (fibroblasts), in accordance with some embodiments.

After the sub-regions are generated (step 320) with the sub-region generation module, representational objects or interest points are determined for each sub-region (step 330) using module 207. In some embodiments, the representational objects are outlines of sub-regions or superpixels pertaining to cells or groups of cells of interest, e.g. fibroblasts or macrophages. In other embodiments, the representational objects are seed points. As noted herein, an objective of the present disclosure is to characterize cells of interest (e.g. irregularly shaped cells) based on sub-regions having similar staining presence, staining intensity, and/or local texture, and to automatically save those homogeneous property sub-regions in a database. The representational objects, or coordinates thereof, are one method of storing the generated sub-regions. FIGS. 9A and 9B provide examples of polygon outlines and center seeds for those superpixels that contain the biological objects of interest.

In some embodiments, algorithms are utilized which create boundaries that separate sub-regions with different colors or textures and that align with dominant edges in the image, such that boundaries are generated which represent biological objects of interest (e.g. irregularly sized or shaped cells such as fibroblasts or macrophages). In some embodiments, a thresholding algorithm (e.g. Outsu, mean clustering, etc.) may be applied to a stain channel image such that sub-regions not having a stain are excluded and only those sub-regions including a threshold amount of stain are provided as a representational objects. In some embodiments, a binary mask of the sub-regions may be generated using a threshold parameter (e.g. a threshold staining parameter provided by an expert pathologist). In some embodiments, segmentation is achieved by applying a series of filters designed to enhance the image such that (i) sub-regions unlikely to represent objects of interest are separated from (ii) sub-regions representing cells having an object of interest. Additional filters may be selectively applied to remove artifacts, remove small blobs, remove small discontinuities, fill holes, and split up bigger blobs.

In some embodiments, regions that are unlikely to have sub-regions identifying irregularly shaped cells are removed, such as by removing image regions in a binary image of the stain channel that are white (corresponding to regions in the tissue samples that are unstained or nearly unstained). In some embodiments, this is achieved by applying a global thresholding filter. Thresholding is a method used for converting an intensity image (I) into a binary image (I') by assigning to all pixels the value one or zero if their intensity is above or below some threshold value, here a global threshold value. In other words, global thresholding is applied to partition pixels depending on their intensity value. In some embodiments, the global thresholding is based on a median and/or standard deviation computed on a first principal component channel, e.g. similar to a gray scale channel. By obtaining the global threshold, it is believed that any white image regions, which are representative of unstained or nearly unstained regions where irregularly shaped cells are likely not present, can be discarded.

In some embodiments, and in the context of the FAP stain, the boundaries may be created by: 1) unmixing the purple channel, 2) thresholding the purple channel to identify FAP-positive regions, 3) applying a superpixel segmentation on the purple channel, and 4) attach feature metrics to the superpixel objects. In some embodiments, the presence of FAP-positive regions may be identified using a supervised-generation rule, which was trained based on ground truth obtained from pathologists. In some embodiments, FAP-positive threshold parameters may be supplied by a pathologist, such as by identifying a threshold on a training set of images. A binary mask may then be generated using the threshold parameters. These methods are further described in Auranuch Lorsakul et al. "Automated whole-slide analysis of multiplex-brightfield IHC images for cancer cells and carcinoma-associated fibroblasts," Proc. SPIE 10140, Medical Imaging 2017: Digital Pathology, 1014007 (2017 Mar. 1), the disclosure of which is hereby incorporated by reference herein in its entirety.

In some embodiments, the boundaries of the sub-regions are traced. For example, an algorithm may be provided which traces the exterior boundary of the sub-regions, as well as those boundaries of "holes" inside or between sub-regions. In some embodiments, the boundaries of the sub-regions are generated by creating the boundary traces using a matlab function called bwboundaries (https://www-.mathworks.com/help/images/ref/bwboundaries.html)

Following boundary creation, the boundary traces were converted into polygon outlines of x,y coordinates. The x,y coordinates of the traced boundaries may be stored in a memory or database, e.g. the row and column coordinates of all of the pixels of the traced border of the sub-region object may be determined and stored.

In some embodiments, seed points are derived by calculating or computing a centroid or center of mass of each sub-region. Methods of determining centroids of irregular objects are known to those of ordinary skill in the art. Once calculated, the centroid of the sub-region is labeled and/or the x,y coordinates of the seed are stored in a memory or database. In some embodiments, the position of the centroid or center of mass may be superimposed on the input image.

Labeling Module

After the sub-regions are generated using the segmentation module 206 and representational objects are computed using module 207, the representational objects are annotated, labeled, or associated with data (step 330), such as the metrics derived from the image analysis module 202 (step 310), using a labeling module 208. The labeling module 208 may create a database 209 which is a non-transitory memory that stores data as noted herein. In some embodiments, the database 209 storages the images received as input, the coordinates of any polygons and/or seed points, and any associated data or labels from image analysis (see FIG. 11).

In that regard, a vector of data may be stored for each segmented sub-region of the image. For example, a vector of data may be stored for each sub-region, including the coordinates of any representational objects and associated image analysis data. By way of example, if the data points "a," "b," and "c" are coordinates for representational objects, and "x," "y," and "z" are metrics (or averages of metrics corresponding to a particular sub-region) derived from image analysis, the database would store the following vectors of data $[a, b, c, x, y, z]^1$, $[a, b, c, x, y, z]^2$, $[a, b, c, x, y, z]^N$, where N is the number of sub-regions generated with segmentation module 206.

In some embodiments, data from the image analysis module describes individual pixels within an image. The skilled artisan will appreciate that the data of all pixels within a particular sub-region may be averaged to provide an average value of the pixel data within the sub-region. For example, individual pixels may each have a certain intensity. The intensity of all of the pixels in a particular sub-region may be averaged to provide an average pixel intensity for that sub-region. That average pixel for that sub-region may be associated with a representational object for that sub-region and the data may be stored together in a memory.

In the context of staining with FAP, the FAP-positive area can be another feature/measurement attached to the super-pixel object. The FAP-positive area refers to the summation of the pixels that have the FAP intensity above a set threshold. The selection of a threshold is described by Auranuch Lorsakul et al. "Automated whole-slide analysis of multiplex-brightfield IHC images for cancer cells and carcinoma-associated fibroblasts," Proc. SPIE 10140, Medical Imaging 2017: Digital Pathology, 1014007 (2017 Mar. 1), the disclosure of which is hereby incorporated by reference herein in its entirety.

As an example of data stored by the labeling module, and in the context of staining a biological sample with the FAP biomarker, an average intensity of the FAP stain within a sub-region may be derived through image analysis for a particular sub-region and that FAP stain intensity may be stored in a database along with the coordinates of any representational objects for that sub-region. Likewise, a particular expression score, such as a FAP expression score, for a sub-region may be derived using image analysis, and that FAP expression score for that sub-region may be stored along with representation objects of that particular sub-region. In addition to average intensity scores and average expression scores for the image portions within any sub-region, other parameters may be stored including, but not limited to, the distances between seed points, the distance between identified tumor cells and irregularly shaped cells (e.g. the distance between a tumor cell and a fibroblast), and FAP-positive areas.

Figure 10A:
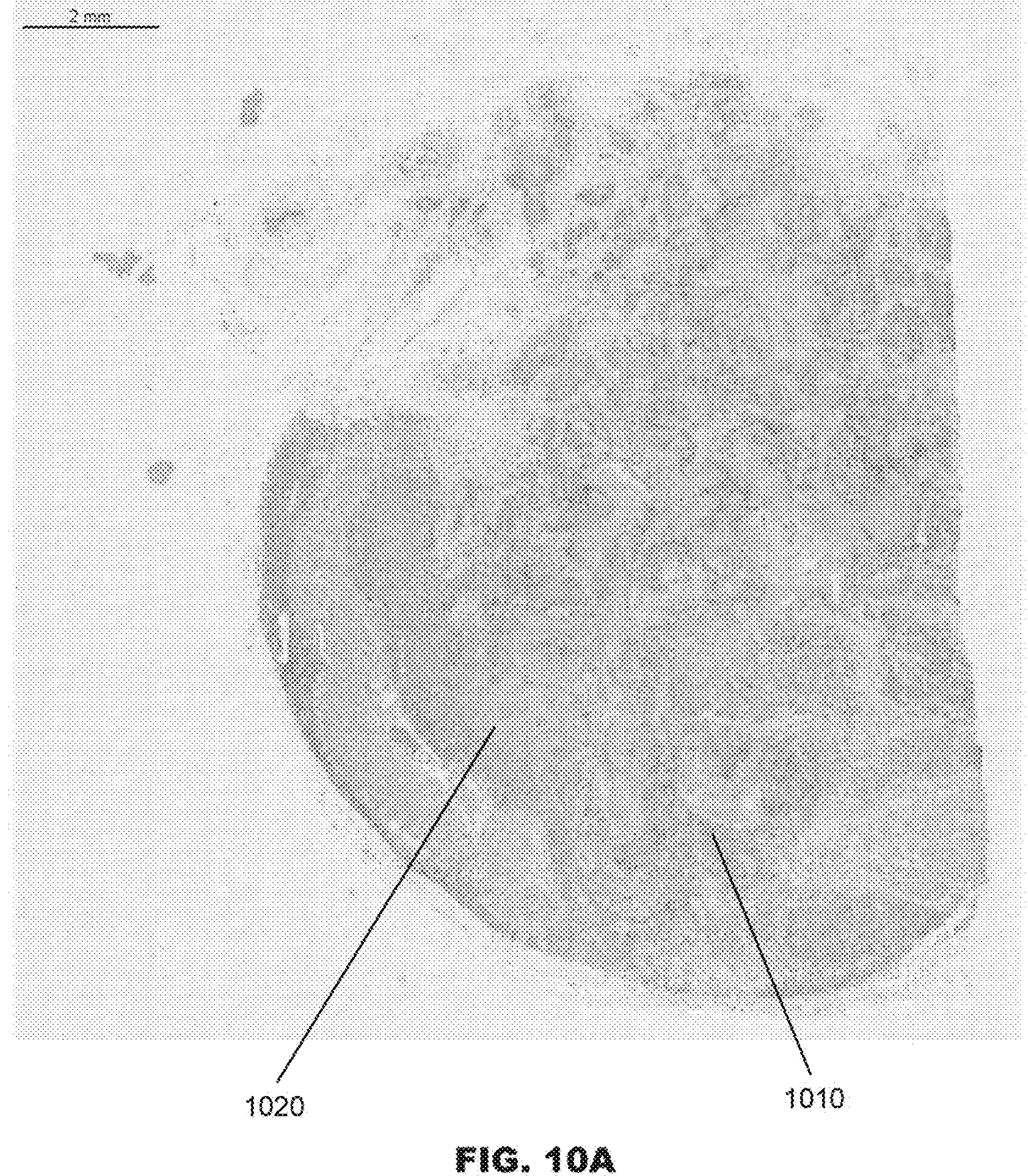
FIG. 10A provides an example of a whole slide IHC image of head-and-neck cancer tissue stained with fibroblast-activation protein (FAP) for fibroblasts (1010) in purple and with pan-cytokeratin (PanCK) for epithelial tumor (1020) in yellow.
Figure 10B:
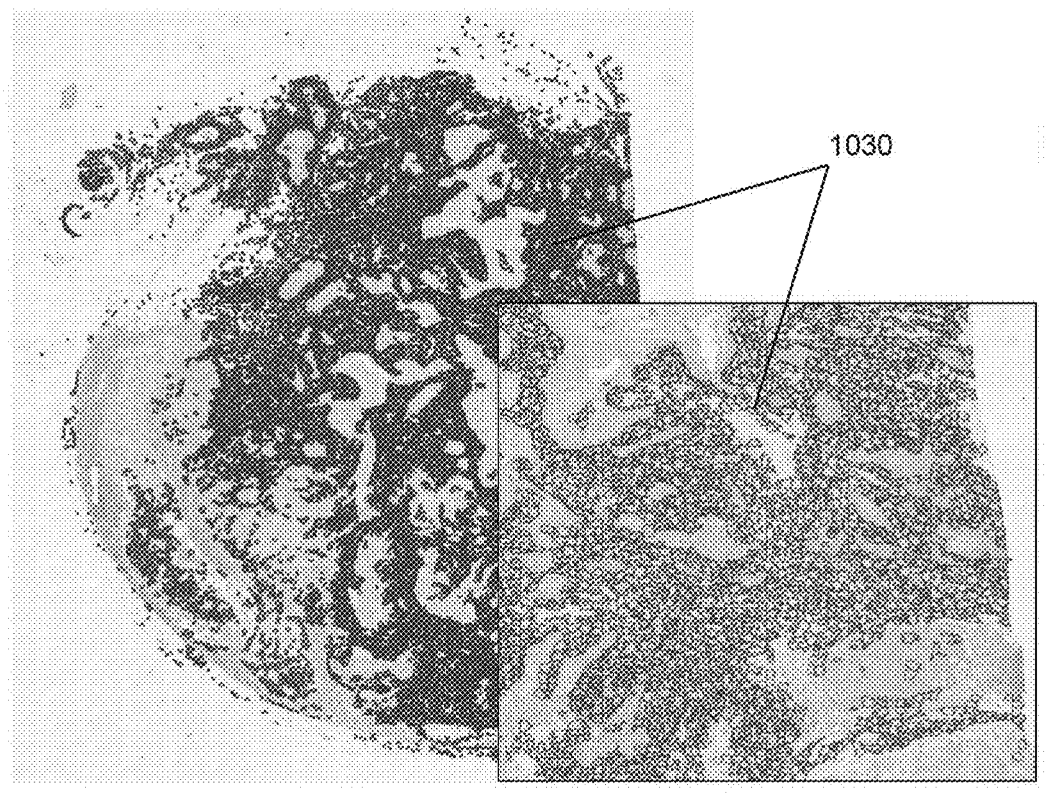
FIG. 10B sets forth an example of polygon outlines attached with their analysis results of the superpixels (blue, 1030) belonging to the fibroblast regions which can be stored in database.
Figure 11:
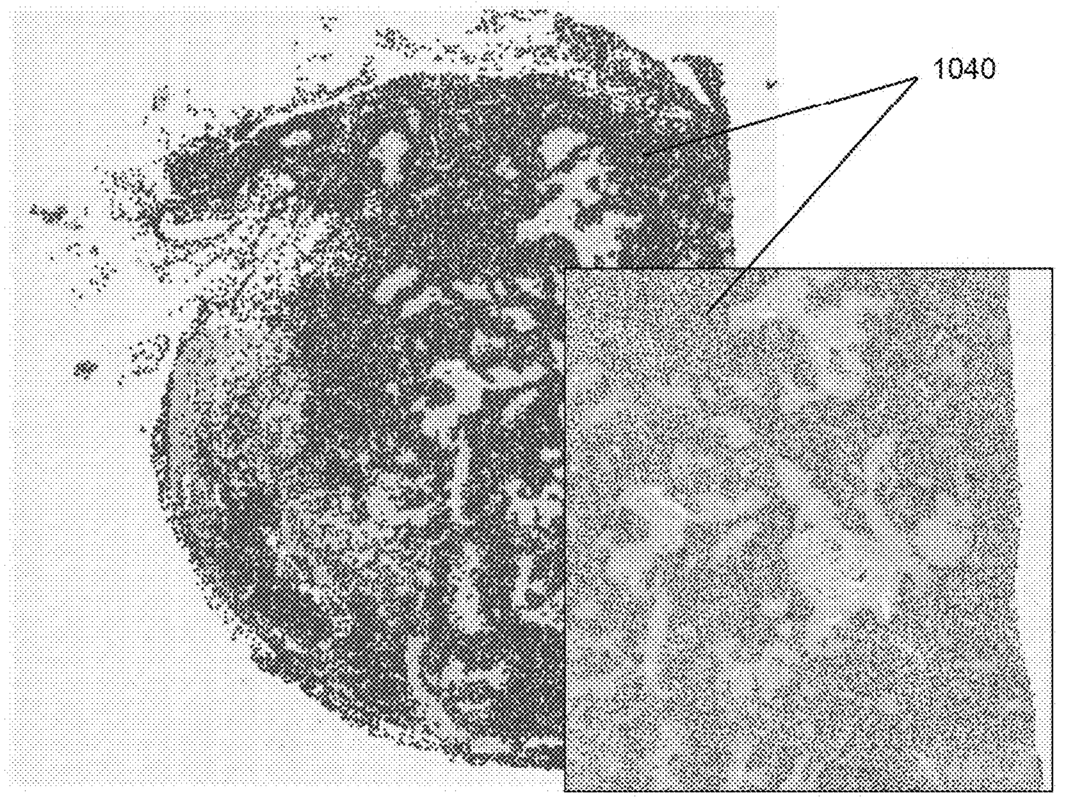
FIG. 11 sets forth an example of center seeds attached with their analysis results of the superpixels (red, 1140) belonging to the fibroblast regions which can be stored in database.

In some embodiments, and by way of example, analysis results, e.g., average local intensity, positive stained area, computed within a corresponding superpixels, are attached to their corresponding polygon outlines and seeds. For a whole slide image, these representation objects (e.g., polygon outlines and seeds) attached with their analysis results are then stored in database in x-y coordinates. FIG. 10A illustrates an example of a whole slide IHC image of head-and-neck cancer tissue stained with fibroblast-activation protein (FAP) for fibroblasts (1010) in purple and with pan-cytokeratin (PanCK) for epithelial tumor (1020) in yellow. FIGS. 10B and 11 show examples of polygon outlines and seeds attached with their analysis results of the superpixels belonging to the fibroblast regions which can be stored in database, respectively.

Data Retrieval or Projection Module

Figure 12:
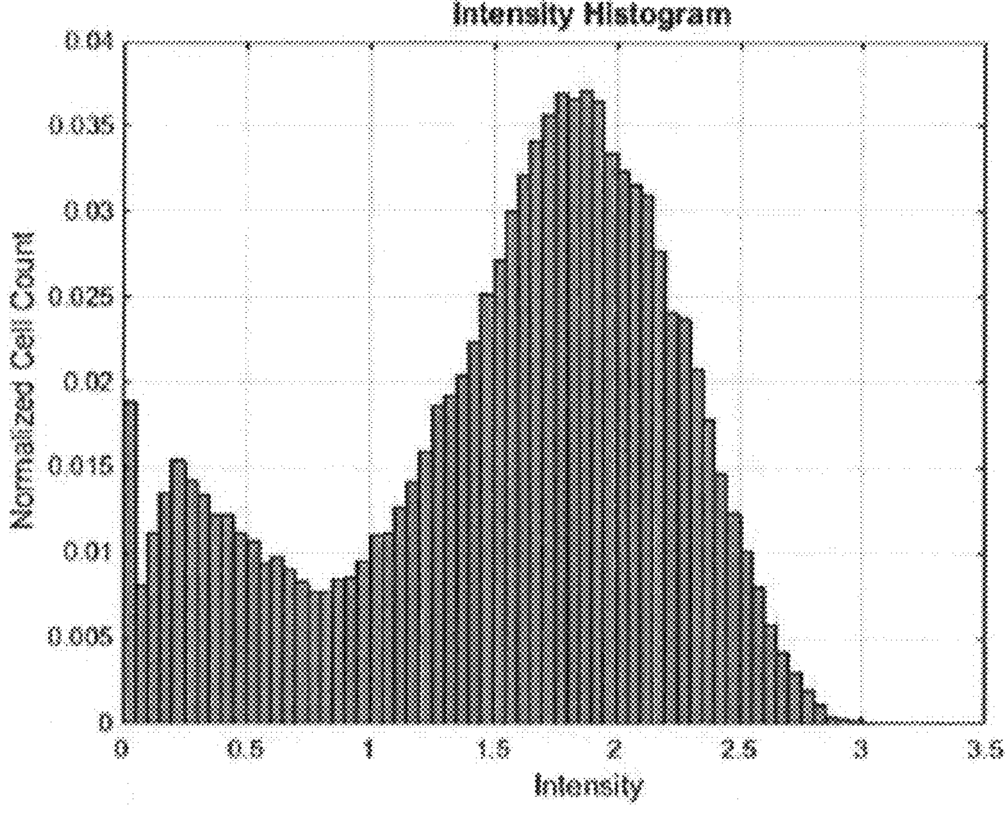
FIG. 12 provides an example of a histogram plot of FAP intensity retrieved from whole slide superpixels.

The skilled artisan will appreciate that the stored analysis results and associated biological features can be later retrieved, and the data may be reported or visualized in various formats, e.g., histogram plot of analysis results. More specifically, the representation object coordinate data and associated image analysis data may be retrieved from the database 209 and used for further analysis. In some embodiments, and by way of example, the representation objects can be retrieved from a database for the visualization or reporting of analysis results within a whole slide image or in user annotated regions. As illustrated in FIG. 12, the associated or attached image analysis results can be reported by plotting in histogram of FAP intensity retrieved from whole slide superpixels. Alternatively, the data can be visualized on a whole-slide image, a field-of-view image, or a portion of an image annotated by a medical professional for further review.

Other Components for Practicing Embodiments of the Present Disclosure

The system 200 of the present disclosure may be tied to a specimen processing apparatus that can perform one or more preparation processes on the tissue specimen. The preparation process can include, without limitation, deparaffinizing a specimen, conditioning a specimen (e.g., cell conditioning), staining a specimen, performing antigen retrieval, performing immunohistochemistry staining (including labeling) or other reactions, and/or performing in situ hybridization (e.g., SISH, FISH, etc.) staining (including labeling) or other reactions, as well as other processes for preparing specimens for microscopy, microanalyses, mass spectrometric methods, or other analytical methods.

The processing apparatus can apply fixatives to the specimen. Fixatives can include cross-linking agents (such as aldehydes, e.g., formaldehyde, paraformaldehyde, and glutaraldehyde, as well as non-aldehyde cross-linking agents), oxidizing agents (e.g., metallic ions and complexes, such as osmium tetroxide and chromic acid), protein-denaturing agents (e.g., acetic acid, methanol, and ethanol), fixatives of unknown mechanism (e.g., mercuric chloride, acetone, and picric acid), combination reagents (e.g., Carnoy's fixative, methacarn, Bouin's fluid, B5 fixative, Rossman's fluid, and Gendre's fluid), microwaves, and miscellaneous fixatives (e.g., excluded volume fixation and vapor fixation).

If the specimen is a sample embedded in paraffin, the sample can be deparaffinized using appropriate deparaffinizing fluid(s). After the paraffin is removed, any number of substances can be successively applied to the specimen. The substances can be for pretreatment (e.g., to reverse protein-crosslinking, expose nucleic acids, etc.), denaturation, hybridization, washing (e.g., stringency wash), detection (e.g., link a visual or marker molecule to a probe), amplifying (e.g., amplifying proteins, genes, etc.), counterstaining, coverslipping, or the like.

The specimen processing apparatus can apply a wide range of substances to the specimen. The substances include, without limitation, stains, probes, reagents, rinses, and/or conditioners. The substances can be fluids (e.g., gases, liquids, or gas/liquid mixtures), or the like. The fluids can be solvents (e.g., polar solvents, non-polar solvents, etc.), solutions (e.g., aqueous solutions or other types of solutions), or the like. Reagents can include, without limitation, stains, wetting agents, antibodies (e.g., monoclonal antibodies, polyclonal antibodies, etc.), antigen recovering fluids (e.g., aqueous- or non-aqueous-based antigen retrieval solutions, antigen recovering buffers, etc.), or the like. Probes can be an isolated nucleic acid or an isolated synthetic oligonucleotide, attached to a detectable label or reporter molecule. Labels can include radioactive isotopes, enzyme substrates, co-factors, ligands, chemiluminescent or fluorescent agents, haptens, and enzymes.

The specimen processing apparatus can be an automated apparatus, such as the BENCHMARK XT instrument and SYMPHONY instrument sold by Ventana Medical Systems, Inc. Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. Published Patent Application Nos. 20030211630 and 20040052685, each of which is incorporated herein by reference in its entirety. Alternatively, specimens can be manually processed.

After the specimens are processed, a user can transport specimen-bearing slides to the imaging apparatus. In some embodiments, the imaging apparatus is a brightfield imager slide scanner. One brightfield imager is the iScan HT and DP200 (Griffin) brightfield scanner sold by Ventana Medical Systems, Inc. In automated embodiments, the imaging apparatus is a digital pathology device as disclosed in International Patent Application No.: PCT/US2010/002772 (Patent Publication No.: WO/2011/049608) entitled IMAGING SYSTEM AND TECHNIQUES or disclosed in U.S. Patent Application No. 61/533,114, filed on Sep. 9, 2011, entitled IMAGING SYSTEMS, CASSETTES, AND METHODS OF USING THE SAME. International Patent Application No. PCT/US2010/002772 and U.S. Patent Application No. 61/533,114 are incorporated by reference in their entities.

The imaging system or apparatus may be a multispectral imaging (MSI) system or a fluorescent microscopy system. The imaging system used here is an MSI. MSI, generally, equips the analysis of pathology specimens with computerized microscope-based imaging systems by providing access to spectral distribution of an image at a pixel level. While there exists a variety of multispectral imaging systems, an operational aspect that is common to all of these systems is a capability to form a multispectral image. A multispectral image is one that captures image data at specific wavelengths or at specific spectral bandwidths across the electromagnetic spectrum. These wavelengths may be singled out by optical filters or by the use of other instruments capable of selecting a pre-determined spectral component including electromagnetic radiation at wavelengths beyond the range of visible light range, such as, for example, infrared (IR).

An MSI system may include an optical imaging system, a portion of which contains a spectrally-selective system that is tunable to define a pre-determined number N of discrete optical bands. The optical system may be adapted to image a tissue sample, illuminated in transmission with a broadband light source onto an optical detector. The optical imaging system, which in one embodiment may include a magnifying system such as, for example, a microscope, has a single optical axis generally spatially aligned with a single optical output of the optical system. The system forms a sequence of images of the tissue as the spectrally selective system is being adjusted or tuned (for example with a computer processor) such as to assure that images are acquired in different discrete spectral bands. The apparatus may additionally contain a display in which appears at least one visually perceivable image of the tissue from the sequence of acquired images. The spectrally-selective system may include an optically-dispersive element such as a diffractive grating, a collection of optical filters such as thin-film interference filters or any other system adapted to select, in response to either a user input or a command of the pre-programmed processor, a particular pass-band from the spectrum of light transmitted from the light source through the sample towards the detector.

An alternative implementation, a spectrally selective system defines several optical outputs corresponding to N discrete spectral bands. This type of system intakes the transmitted light output from the optical system and spatially redirects at least a portion of this light output along N spatially different optical paths in such a way as to image the sample in an identified spectral band onto a detector system along an optical path corresponding to this identified spectral band.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus. Any of the modules described herein may include logic that is executed by the processor (s). "Logic," as used herein, refers to any information having the form of instruction signals and/or data that may be applied to affect the operation of a processor. Software is an example of logic.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or can be included in, one or more separate physical components or media (e.g., multiple CDs, disks, or other storage devices). The operations described in this specification can be implemented as operations performed by a data processing apparatus on data stored on one or more computer-readable storage devices or received from other sources.

The term "programmed processor" encompasses all kinds of apparatus, devices, and machines for processing data, including by way of example a programmable microprocessor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus also can include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., an LCD (liquid crystal display), LED (light emitting diode) display, or OLED (organic light emitting diode) display, for displaying information to the user and a keyboard and a pointing device, e.g., a mouse or a trackball, by which the user can provide input to the computer. In some implementations, a touch screen can be used to display information and receive input from a user. Other kinds of devices can be used to provide for interaction with a user as well; for example, feedback provided to the user can be in any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks). For example, the network 20 of FIG. 1 can include one or more local area networks.

The computing system can include any number of clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

Additional Methods of Unmixing/Optional Unmixing Module

Unmixing is the procedure by which the measured spectrum of a mixed pixel is decomposed into a collection of constituent spectra, or endmembers, and a set of corresponding fractions, or abundances, that indicate the proportion of each endmember present in the pixel. Specifically, the unmixing process can extract stain-specific channels to determine local concentrations of individual stains using reference spectra that are well known for standard types of tissue and stain combinations. The unmixing may use reference spectra retrieved from a control image or estimated from the image under observation. Unmixing the component signals of each input pixel enables retrieval and analysis of stain-specific channels, such as a hematoxylin channel and an eosin channel in H&E images, or a diaminobenzidine (DAB) channel and a counterstain (e.g., hematoxylin) channel in IHC images. The terms "unmixing" and "color deconvolution" (or "deconvolution") or the like (e.g. "deconvolving," "unmixed") are used interchangeably in the art. In some embodiments, the multiplex images are unmixed with an unmixing module using liner unmixing. Linear unmixing is described, for example, in 'Zimmermann "Spectral Imaging and Linear Unmixing in Light Microscopy" Adv Biochem Engin/Biotechnol (2005) 95:245-265' and in in C. L. Lawson and R. J. Hanson, "Solving least squares Problems", PrenticeHall, 1974, Chapter 23, p. 161,' the disclosures of which are incorporated herein by reference in their entirety. In linear stain unmixing, the measured spectrum (S(λ)) at any pixel is considered a linear mixture of stain spectral components and equals the sum of the proportions or weights (A) of each individual stain's color reference (R(λ)) that is being expressed at the pixel $$S(\lambda) = A_1 \cdot R_1(\lambda) + A_2 \cdot R_2(\lambda) + A_3 \cdot R_3(\lambda) \ \ldots \ \ldots \ A_i \cdot R_i(\lambda)$$

which can be more generally expressed as in matrix form as $$S(\lambda) = \Sigma A_i \cdot R_i(\lambda) \text{ or } S = R \cdot A$$

If there are M channels images acquired and N individual stains, the columns of the M×N matrix R are the optimal color system as derived herein, the N×1 vector A is the unknown of the proportions of individual stains and the M×1 vector S is the measured multichannel spectral vector at a pixel. In these equations, the signal in each pixel (S) is measured during acquisition of the multiplex image and the reference spectra, i.e. the optimal color system, is derived as described herein. The contributions of various stains ($A_i$) can be determined by calculating their contribution to each point in the measured spectrum. In some embodiments, the solution is obtained using an inverse least squares fitting approach that minimizes the square difference between the measured and calculated spectra by solving the following set of equations, $$[\partial \Sigma_j\{S(\lambda_j) - \Sigma_i A_i \cdot R_i(\lambda_j)\}2]/\partial A_i = 0$$

In this equation, j represents the number of detection channels and i equals the number of stains. The linear equation solution often involves allowing a constrained unmixing to force the weights (A) to sum to unity.

In other embodiments, unmixing is accomplished using the methods described in WO2014/195193, entitled "Image Adaptive Physiologically Plausible Color Separation," filed on May 28, 2014, the disclosure of which is hereby incorporated by reference in its entirety herein. In general, WO2014/195193 describes a method of unmixing by separating component signals of the input image using iteratively optimized reference vectors. In some embodiments, image data from an assay is correlated with expected or ideal results specific to the characteristics of the assay to determine a quality metric. In the case of low quality images or poor correlations against ideal results, one or more reference column vectors in matrix R are adjusted, and the unmixing is repeated iteratively using adjusted reference vectors, until the correlation shows a good quality image that matches physiological and anatomical requirements. The anatomical, physiological, and assay information may be used to define rules that are applied to the measured image data to determine the quality metric. This information includes how the tissue was stained, what structures within the tissue were intended or not intended to be stained, and relationships between structures, stains, and markers specific to the assay being processed. An iterative process results in stain-specific vectors that can generate images that accurately identify structures of interest and biologically relevant information, are free from any noisy or unwanted spectra, and therefore fit for analysis. The reference vectors are adjusted to within a search space. The search space defines a range of values that a reference vector can take to represent a stain. The search space may be determined by scanning a variety of representative training assays including known or commonly occurring problems, and determining high-quality sets of reference vectors for the training assays.

In other embodiments, unmixing is accomplished using the methods described in WO2015/124772, entitled "Group Sparsity Model for Image Unmixing," filed on Feb. 23, 2015, the disclosure of which is hereby incorporated by reference in its entirety herein. In general, WO2015/124772 describes unmixing using a group sparsity framework, in which fractions of stain contributions from a plurality of colocation markers are modeled within a "same group" and fractions of stain contributions from a plurality of non-colocation markers are modeled in different groups, providing co-localization information of the plurality of colocation markers to the modeled group sparsity framework, solving the modeled framework using a group lasso to yield a least squares solution within each group, wherein the least squares solution corresponds to the unmixing of the colocation markers, and yielding a sparse solution among the groups that corresponds to the unmixing of the non-colocation markers. Moreover, WO2015124772 describes a method of unmixing by inputting image data obtained from the biological tissue sample, reading reference data from an electronic memory, the reference data being descriptive of the stain color of each one of the multiple stains, reading colocation data from electronic memory, the colocation data being descriptive of groups of the stains, each group comprising stains that can be collocated in the biological tissue sample, and each group forming a group for the group lasso criterion, at least one of the groups having a size of two or above, and calculating a solution of the group lasso criterion for obtaining the unmixed image using the reference data as a reference matrix. In some embodiments, the method for unmixing an image may comprise generating a group sparsity model wherein a fraction of a stain contribution from colocalized markers is assigned within a single group and a fraction of a stain contribution from non-colocalized markers is assigned within separate groups, and solving the group sparsity model using an unmixing algorithm to yield a least squares solution within each group.

Example—A Comparison of the FAP-Positive Area Between the High-Resolution and Mid-Resolution Analysis Methods The experiment was performed to compare the accuracy of FAP-positive area results using:

1) A FAP-positive high-resolution analysis. For this measurement, all FAP-positive pixels after thresholding at a high magnification (20×) were accumulated with a spatial resolution of 0.465-micrometer pixel size. Then, the reporting areas selected from the pre-annotated regions were obtained as a pixel-by-pixel FAP-positive area for the regions of interest.
2) Within the pre-annotated regions, the FAP-positive areas measured using the mid-resolution analysis approach described herein, which were calculated by summing the FAP-positive area of the FAP-superpixel objects, seeds, or polygon outlines.

Figure 14:
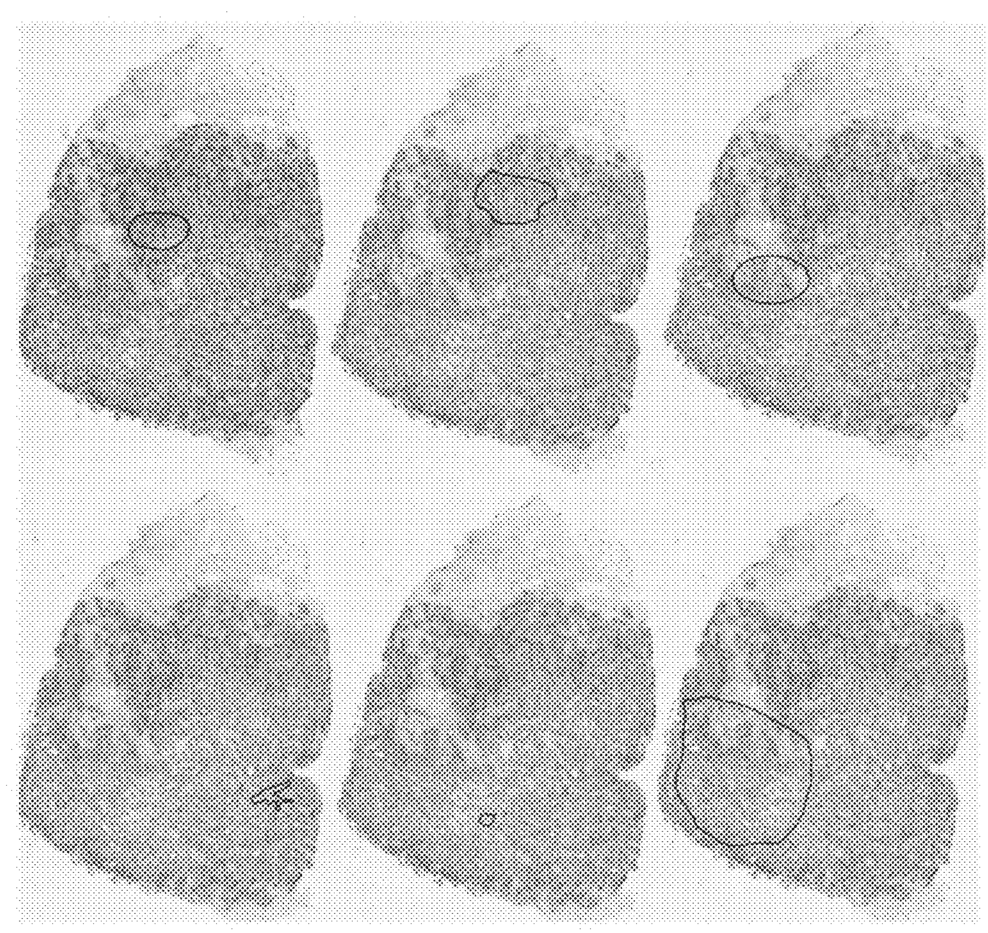
FIG. 14 sets forth six different annotation shapes and regions within an image of a biological sample.
Figure 15:
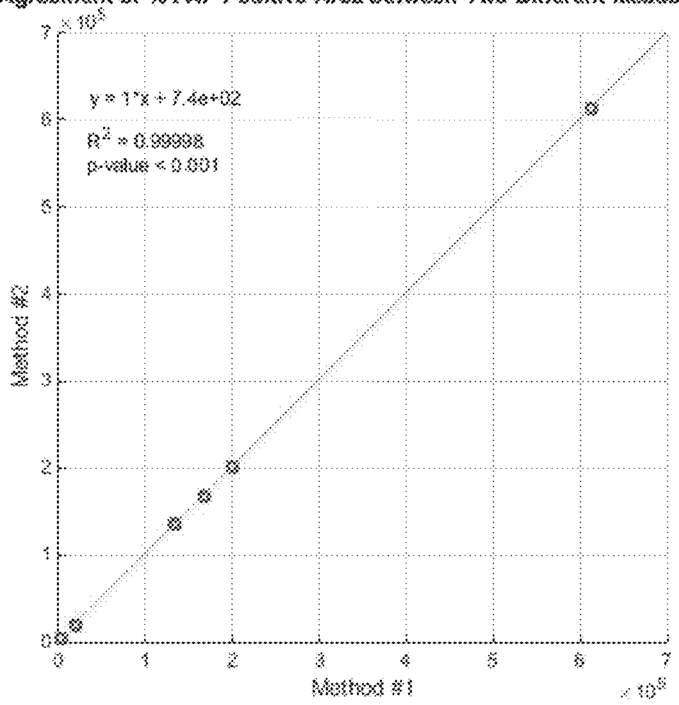
FIG. 15 illustrates the agreement of the percentage of the FAP-positive areas between (i) the FAP+ area determined using a high-resolution analysis approach and (ii) using the example mid-resolution (sub-regional) approaches described herein.

Six different annotated areas (see FIG. 14), each having different shapes (large, small, round or strangely shaped, etc.), were analyzed according to both methods. As shown in FIG. 15 and in the table which follows, there was no significant difference ($R^2=0.99$, $p<0.001$) between the comparison results of the FAP-positive area measured using these two methods.

FAP-Positive Area Measurement in Different Annotations in Slide 15-020499

| Annotation | Method #1 | Method #2 | NID |
|---|---|---|---|
| 1 | 1.68E+05 | 1.68E+05 | 40958 |
| 2 | 2.00E+05 | 2.02E+05 | 229850 |
| 3 | 1.33E+05 | 1.35E+05 | 229865 |
| 4 | 1.94E+04 | 1.97E+04 | 229873 |
| 5 | 3.38E+03 | 3.63E+03 | 229886 |
| 6 | 6.12E+05 | 6.13E+05 | 229890 |

Method #1 - Measurement using the FAP+ high resolution result image
Method #2- Measurement by summing of the attached features FAP+ area of FAP seeds In a conclusion, when we summed the area features computed within superpixels in a specific annotation, the summation of the area is equal to the area we calculated directly using the high-resolution analysis approach within that annotation. The results of FAP-positive area show no significant difference computed between the two methods (with and without superpixels) with different shapes of annotated regions.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

Although the present disclosure has been described with reference to a number of illustrative embodiments, it should be understood that numerous other modifications and embodiments can be devised by those skilled in the art that will fall within the spirit and scope of the principles of this disclosure. More particularly, reasonable variations and modifications are possible in the component parts and/or arrangements of the subject combination arrangement within the scope of the foregoing disclosure, the drawings, and the appended claims without departing from the spirit of the disclosure. In addition to variations and modifications in the component parts and/or arrangements, alternative uses will also be apparent to those skilled in the art.

Additional Embodiments

Additional Embodiment 1. A method of storing image analysis data derived from an image of a biological specimen having at least one stain, the method comprising:

(a) deriving one or more feature metrics from the image;
(b) segmenting the image into a plurality of sub-regions, each sub-region comprising pixels that are substantially uniform in at least one of staining presence, staining intensity, or local texture;
(c) generating a plurality of representational objects based on the plurality of segmented sub-regions;
(d) associating each of the plurality of representational objects with the derived feature metrics; and
(e) storing coordinates for each representational object along with the associated derived feature metrics in a database.

Additional Embodiment 2. The method of additional embodiment 1, wherein the segmentation of the image into the plurality of sub-regions comprises deriving superpixels.

Additional Embodiment 3. The method of additional embodiment 2, wherein the superpixels are derived by (i) grouping pixels with local k-means clustering; and (ii) using a connected components algorithm to merge small isolated regions into nearest large superpixels.

Additional Embodiment 4. The method of any of additional embodiments 1 to 3, wherein the segmentation of the image into the plurality of sub-regions comprises overlaying a sampling grid onto the image, the sampling grid defining non-overlapping areas having a predetermined size and shape.

Additional Embodiment 5. The method of any of additional embodiments 1 to 4, wherein the sub-regions have a M×N size, where M ranges from 50 pixels to 100 pixels, and where N ranges from 50 pixels to about 100 pixels.

Additional Embodiment 6. The method of any of additional embodiments 1 to 5, wherein the representational objects comprise outlines of sub-regions that meet a predefined staining intensity threshold.

Additional Embodiment 7. The method of any of additional embodiments 1 to 6, wherein the representational objects comprise seed points.

Additional Embodiment 8. The method of additional embodiment 7, wherein the seed points are derived by computing a centroid for each of the plurality of sub-regions.

Additional Embodiment 9. The method of additional embodiment 6, wherein the derived feature metrics comprise staining intensities, and wherein an average staining intensity for all pixels within each generated representational object outline is computed.

Additional Embodiment 10. The method of additional embodiments 1 to 7, wherein the derived feature metrics comprise expression scores, and wherein average expression scores corresponding to areas within each generated sub-region are associated with the generated plurality of representational objects.

Additional Embodiment 11. The method of any of additional embodiments 1 to 7, further comprising retrieving the stored coordinates and associated feature metric data from the database, and projecting the retrieved data onto the image.

Additional Embodiment 12. A system for deriving data corresponding to irregularly-shaped cells from an image of a biological sample comprising at least one stain, the system comprising: (i) one or more processors, and (ii) a memory coupled to the one or more processors, the memory to store computer-executable instructions that, when executed by the one or more processors, cause the system to perform operations comprising:

(a) deriving one or more feature metrics from the image;
(b) generating a plurality of sub-regions within the image, each sub-region having pixels with similar characteristics, the characteristics selected from color, brightness, and/or texture;
(c) computing a series of representational objects based on the generated plurality of sub-regions; and
(d) associating the derived one or more feature metrics from the image with calculated coordinates of each of the series of computed representational objects.

Additional Embodiment 13. The system of additional embodiment 12, wherein the segmentation of the image into the plurality of sub-regions comprises deriving superpixels.

Additional Embodiment 14. The system of any of additional embodiments 12 to 13, wherein the superpixels are derived using one of a graph-based approach or a gradient-ascent-based approach.

Additional Embodiment 15. The system of any of additional embodiments 12 to 14, wherein the superpixels are derived by (i) grouping pixels with local k-means clustering; and (ii) using a connected components algorithm to merge small isolated regions into nearest large superpixels.

Additional Embodiment 16. The system of any of additional embodiments 12 to 15, wherein the representational objects comprise outlines of sub-regions that meet a predefined staining intensity threshold.

Additional Embodiment 17. The system of any of additional embodiments 12 to 16, wherein the representational objects comprise seed points.

Additional Embodiment 18. The system of any of additional embodiments 12 to 17, wherein the operations further comprise storing the derived one or more feature metrics and associated calculated representational object coordinates in a database.

Additional Embodiment 19. The system of any of additional embodiments 12 to 18, wherein the one or more derived feature metrics comprise at least one expression score selected from percent positivity, an H-score, and a staining intensity.

Additional Embodiment 20. The system any of additional embodiments 12 to 19, wherein data corresponding to irregularly-shaped cells is derived for a region-of-interest within the image.

Additional Embodiment 21. The system of additional embodiment 20, wherein the region-of-interest is an area of the image annotated by a medical professional.

Additional Embodiment 22. A non-transitory computer-readable medium storing instructions for analyzing data associated with biological objects having irregular shapes, the instructions comprising:

(a) instructions for deriving one or more feature metrics from an image of a biological sample, the biological sample comprising at least one stain;

(b) instructions for partitioning the image into a series of sub-regions by grouping pixels having similar characteristics, the characteristics selected from color, brightness, and/or texture;

(c) instructions for computing a plurality of representational objects based on the series of partitioned sub-regions; and (d) instructions for associating the derived one or more feature metrics from the image with calculated coordinates of each of the plurality of computed representational objects.

Additional Embodiment 23. The non-transitory computer-readable medium of additional embodiment 22, wherein the partitioning of the image into the series of sub-regions comprises computing superpixels.

Additional Embodiment 24. The non-transitory computer-readable medium of any of additional embodiments 22 to 23, wherein the superpixels are computed using one of a normalized cuts algorithm, an agglomerative clustering algorithm, a quick shift algorithm, a turbopixel algorithm, or simple linear iterative clustering algorithm.

Additional Embodiment 25. The non-transitory computer-readable medium of any of additional embodiments 22 to 24, wherein the superpixels are generated using simple iterative clustering, and wherein a superpixel size parameter is set to between about 40 pixels and about 400 pixels, and wherein a compactness parameter is set to between about 10 to about 100.

Additional Embodiment 26. The non-transitory computer-readable medium of any of additional embodiments 22 to 25, wherein the superpixels are computed by (i) grouping pixels with local k-means clustering; and (ii) using a connected components algorithm to merge small isolated regions into nearest large superpixels.

Additional Embodiment 27. The non-transitory computer-readable medium of additional embodiments 22 to 26, wherein the biological sample is stained with at least FAP, and wherein the derived one or more feature metrics include at least one of a FAP staining intensity or a FAP percent positivity.

Additional Embodiment 28. The non-transitory computer-readable medium of additional embodiment 27, wherein an average FAP percent positivity is calculated for all pixels within a sub-region.

Additional Embodiment 29. The non-transitory computer-readable medium of additional embodiment 27, wherein an average FAP staining intensity is calculated for all pixels within a sub-region.

Additional Embodiment 30. The non-transitory computer-readable medium of any of additional embodiments 22 to 26, wherein the representational objects comprise at least one of polygon outlines and seed points.

Additional Embodiment 31. The non-transitory computer-readable medium of any of additional embodiments 22 to 26, further comprising instructions for storing the derived one or more feature metrics and associated calculated representational object coordinates in a database.

Additional Embodiment 32. The non-transitory computer-readable medium of additional embodiment 31, further comprising instructions for projecting stored information onto the image of the biological sample.

The invention claimed is:

1. A method comprising:

accessing an image of a biological sample stained with at least one stain, wherein a portion of the image corresponds to a first characteristic of the at least one stain and a portion of the image corresponds to a second characteristic of the at least one stain;

deriving a set of feature metrics from the image, wherein the set of feature metrics is derived based on cell nuclei depicted by the image;

segmenting the image into a plurality of sub-regions, wherein each sub-region of the plurality of sub-regions defines a region of interest within the image, wherein at least one sub-region of the plurality of sub-regions is a superpixel corresponding to pixels of the image associated with the first characteristic, and wherein at least one sub-region of the plurality of sub-regions is a superpixel corresponding to pixels of the image associated with the second characteristic;

determining one or more representational objects for each sub-region of the plurality of sub-regions; and associating, for each sub-region of the plurality of sub-regions, coordinates for each representational object of the one or more representational objects determined for the respective sub-region and a subset of feature metrics of the set of feature metrics, the subset of feature metrics derived from a portion of the image that corresponds to the respective sub-region.

2. The method of claim 1, wherein each representational object of the one or more representational objects determined for each sub-region of the plurality of sub-regions corresponds to a particular cell type of a plurality of cell types.

3. The method of claim 2, wherein the plurality of cell types comprises a fibroblast cell type and a macrophage cell type.

4. The method of claim 1, wherein each sub-region of the plurality of sub-regions comprises a set of pixels of the image arranged in a predefined shape.

5. The method of claim 1, wherein segmenting the image into a plurality of sub-regions comprises grouping pixels of the image into superpixels.

6. The method of claim 1, wherein segmenting the image into a plurality of sub-regions comprises iteratively applying a series of filters to the image.

7. The method of claim 1, wherein determining the one or more representational objects comprises identifying sub-regions of the plurality of sub-regions that represent objects of interests.

8. A system comprising:

(i) one or more processors, and (ii) a memory coupled to the one or more processors, the memory storing computer-executable instructions which, when executed by the one or more processors, cause the system to perform operations comprising:

accessing an image of a biological sample stained with at least one stain, wherein a portion of the image corresponds to a first characteristic of the at least one stain and a portion of the image corresponds to a second characteristic of the at least one stain;

deriving a set of feature metrics from the image, wherein the set of feature metrics is derived based on cell nuclei depicted by the image;

segmenting the image into a plurality of sub-regions, wherein each sub-region of the plurality of sub-regions defines a region of interest within the image, wherein at least one sub-region of the plurality of sub-regions is a superpixel corresponding to pixels of the image associated with the first characteristic, and wherein at least one sub-region of the plurality of sub-regions is a superpixel corresponding to pixels of the image associated with the second characteristic;

determining one or more representational objects for each sub-region of the plurality of sub-regions; and associating, for each sub-region of the plurality of sub-regions, coordinates for each representational object of the one or more representational objects determined for the respective sub-region and a subset of feature metrics of the set of feature metrics, the subset of feature metrics derived from a portion of the image that corresponds to the respective sub-region.

9. The system of claim 8, wherein each representational object of the one or more representational objects determined for each sub-region of the plurality of sub-regions corresponds to a particular cell type of a plurality of cell types.

10. The system of claim 9, wherein the plurality of cell types comprises a fibroblast cell type and a macrophage cell type.

11. The system of claim 8, wherein each sub-region of the plurality of sub-regions comprises a set of pixels of the image arranged in a predefined shape.

12. The system of claim 8, wherein segmenting the image into a plurality of sub-regions comprises grouping pixels of the image into superpixels.

13. The system of claim 8, wherein segmenting the image into a plurality of sub-regions comprises iteratively applying a series of filters to the image.

14. The system of claim 8, wherein determining the one or more representational objects comprises identifying sub-regions of the plurality of sub-regions that represent objects of interests.

15. A non-transitory computer-readable medium storing computer-readable instructions which, when executed by one or more processors, cause a system to perform operations comprising:

accessing an image of a biological sample stained with at least one stain, wherein a portion of the image corresponds to a first characteristic of the at least one stain and a portion of the image corresponds to a second characteristic of the at least one stain;

deriving a set of feature metrics from the image, wherein the set of feature metrics is derived based on cell nuclei depicted by the image;

segmenting the image into a plurality of sub-regions, wherein each sub-region of the plurality of sub-regions defines a region of interest within the image, wherein at least one sub-region of the plurality of sub-regions is a superpixel corresponding to pixels of the image associated with the first characteristic, and wherein at least one sub-region of the plurality of sub-regions is a superpixel corresponding to pixels of the image associated with the second characteristic;

determining one or more representational objects for each sub-region of the plurality of sub-regions; and associating, for each sub-region of the plurality of sub-regions, coordinates for each representational object of the one or more representational objects determined for the respective sub-region and a subset of feature metrics of the set of feature metrics, the subset of feature metrics derived from a portion of the image that corresponds to the respective sub-region.

16. The non-transitory computer-readable media of claim 15, wherein each representational object of the one or more representational objects determined for each sub-region of the plurality of sub-regions corresponds to a particular cell type of a plurality of cell types.

17. The non-transitory computer-readable media of claim 15, wherein each sub-region of the plurality of sub-regions comprises a set of pixels of the image arranged in a predefined shape.

18. The non-transitory computer-readable media of claim 15, wherein segmenting the image into a plurality of sub-regions comprises grouping pixels of the image into superpixels.

19. The non-transitory computer-readable media of claim 15, wherein segmenting the image into a plurality of sub-regions comprises iteratively applying a series of filters to the image.

20. The non-transitory computer-readable media of claim 15, wherein determining the one or more representational objects comprises identifying sub-regions of the plurality of sub-regions that represent objects of interests.

* * * * *